(12) United States Patent
Gawtrey et al.

(10) Patent No.: US 7,485,289 B2
(45) Date of Patent: *Feb. 3, 2009

(54) COSMETIC COMPOSITIONS CONTAINING A PARTICULAR AMINOSILICONE AND A CONDITIONER, AND USES THEREOF

(75) Inventors: Jonathan Gawtrey, Boulogne (FR); Serge Restle, Saint-Prix (FR); Sandrine Decoster, Saint Gratien (FR); Pascale Lazzeri, Levallois Perret (FR)

(73) Assignee: L'Oreal, S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/706,399

(22) Filed: Feb. 15, 2007

(65) Prior Publication Data

US 2007/0154441 A1    Jul. 5, 2007

Related U.S. Application Data

(62) Division of application No. 10/290,409, filed on Nov. 8, 2002, now Pat. No. 7,223,385.

(30) Foreign Application Priority Data

Nov. 8, 2001 (FR) .................................. 01 14476
Nov. 8, 2001 (FR) .................................. 01 14477

(51) Int. Cl.
*A61Q 5/12* (2006.01)
*A61Q 5/02* (2006.01)

(52) U.S. Cl. .............................. 424/70.12; 424/70.1

(58) Field of Classification Search ............... None
See application file for complete search history.

(56) References Cited

U.S. PATENT DOCUMENTS

| | | |
|---|---|---|
| 2,047,398 A | 7/1936 | Voss et al. |
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 10/1950 | Mannheimer |
| 2,723,248 A | 11/1955 | Wright |
| 2,781,354 A | 2/1957 | Mannheimer |
| 2,798,053 A | 7/1957 | Brown |
| 2,923,692 A | 2/1960 | Ackerman et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,810,977 A | 5/1974 | Levine et al. |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,990,459 A | 11/1976 | Papantoniou |
| 4,001,432 A | 1/1977 | Green et al. |
| 4,005,193 A | 1/1977 | Green et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,070,533 A | 1/1978 | Papantoniou et al. |
| 4,075,136 A | 2/1978 | Schaper |
| 4,076,912 A | 2/1978 | Papantoniou et al. |
| 4,128,631 A | 12/1978 | Lundmark et al. |
| 4,129,711 A | 12/1978 | Viout et al. |
| 4,131,576 A | 12/1978 | Iovine et al. |
| 4,137,208 A | 1/1979 | Elliott |
| 4,157,388 A | 6/1979 | Christiansen |
| 4,165,367 A | 8/1979 | Chakrabarti |

(Continued)

FOREIGN PATENT DOCUMENTS

AU    200039428    2/2001

(Continued)

OTHER PUBLICATIONS

Patrick D. Dorgan et al., "Waxes in Cosmetics," Drug & Cosmetic Industry, Dec. 1983, pp. 30-33.

(Continued)

*Primary Examiner*—Jyothsna A Venkat
(74) *Attorney, Agent, or Firm*—Finnegan, Henderson, Farabow, Garrett, & Dunner, L.L.P.

(57) ABSTRACT

A novel cosmetic composition comprising, in a cosmetically acceptable medium, at least one aminosilicone as defined herein having, for example, a contact angle with water ranging from 90° to 180° and at least one conditioner, being able to afford, for example, at least one improved cosmetic property (such as lightness, disentangling, volume and sheen) and/or at least one of long-lasting and remanent effects, as well as uses of the composition, such as for washing and/or conditioning keratin materials such as the hair or the skin.

33 Claims, No Drawings

U.S. PATENT DOCUMENTS

| | | | |
|---|---|---|---|
| 4,172,887 A | 10/1979 | Vanlerberghe et al. | |
| 4,217,914 A | 8/1980 | Jacquet et al. | |
| 4,223,009 A | 9/1980 | Chakrabarti | |
| 4,237,243 A | 12/1980 | Quack et al. | |
| 4,277,581 A | 7/1981 | Vanlerberghe et al. | |
| 4,282,203 A | 8/1981 | Jacquet et al. | |
| 4,349,532 A | 9/1982 | Vanlerberghe et al. | |
| 4,459,285 A * | 7/1984 | Grollier et al. | 424/74 |
| 4,509,949 A | 4/1985 | Huang et al. | |
| 4,591,610 A | 5/1986 | Grollier | |
| 4,608,250 A | 8/1986 | Jacquet et al. | |
| 4,673,568 A | 6/1987 | Grollier et al. | |
| 4,693,935 A | 9/1987 | Mazurek | |
| 4,702,906 A | 10/1987 | Jacquet et al. | |
| 4,710,314 A | 12/1987 | Madrange et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,770,873 A | 9/1988 | Wolfram et al. | |
| 4,839,166 A | 6/1989 | Grollier et al. | |
| 4,957,732 A | 9/1990 | Grollier et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,057,311 A | 10/1991 | Kamegai et al. | |
| 5,061,289 A | 10/1991 | Clausen et al. | |
| 5,077,040 A | 12/1991 | Bergmann et al. | |
| 5,085,860 A | 2/1992 | Junino et al. | |
| 5,089,252 A | 2/1992 | Grollier et al. | |
| 5,106,612 A | 4/1992 | Maignan et al. | |
| 5,139,037 A | 8/1992 | Grollier et al. | |
| 5,154,918 A | 10/1992 | Maignan et al. | |
| 5,196,189 A | 3/1993 | Jacquet et al. | |
| 5,210,324 A | 5/1993 | Farrar et al. | |
| 5,340,367 A | 8/1994 | Schultz et al. | |
| 5,344,464 A | 9/1994 | Madrange et al. | |
| 5,380,340 A | 1/1995 | Neunhoeffer et al. | |
| 5,466,878 A | 11/1995 | Junino et al. | |
| 5,534,267 A | 7/1996 | Neunhoeffer et al. | |
| 5,538,717 A | 7/1996 | La Poterie | |
| 5,583,257 A | 12/1996 | Junino et al. | |
| 5,626,840 A | 5/1997 | Thomaides et al. | |
| 5,663,366 A | 9/1997 | Neunhoeffer et al. | |
| 5,708,151 A | 1/1998 | Mockli | |
| 5,741,337 A | 4/1998 | Bone et al. | |
| 5,756,076 A | 5/1998 | Cervantes et al. | |
| 5,766,576 A | 6/1998 | Lowe et al. | |
| 5,773,611 A | 6/1998 | Zysman et al. | |
| 5,833,997 A | 11/1998 | Mahieu et al. | |
| 5,925,341 A | 7/1999 | Cervantes et al. | |
| 5,958,392 A | 9/1999 | Grollier et al. | |
| 5,976,195 A | 11/1999 | De La Mettrie et al. | |
| 6,010,541 A | 1/2000 | De La Mettrie | |
| 6,071,504 A | 6/2000 | Kawai et al. | |
| 6,099,592 A | 8/2000 | Vidal et al. | |
| 6,099,593 A | 8/2000 | Terranova et al. | |
| 6,143,286 A | 11/2000 | Bhambhani et al. | |
| 6,177,090 B1 | 1/2001 | Dubief et al. | |
| 6,179,881 B1 | 1/2001 | Henrion et al. | |
| 6,214,326 B1 | 4/2001 | Dupuis | |
| 6,254,646 B1 | 7/2001 | De La Mettrie et al. | |
| 6,260,556 B1 | 7/2001 | Legrand et al. | |
| 6,284,003 B1 | 9/2001 | Rose et al. | |
| 6,319,959 B1 | 11/2001 | Mougin et al. | |
| 6,372,876 B1 | 4/2002 | Kim et al. | |
| 6,395,265 B1 | 5/2002 | Mougin et al. | |
| 6,471,953 B1 | 10/2002 | N'Guyen et al. | |
| 6,479,042 B1 | 11/2002 | N'Guyen et al. | |
| 6,506,373 B1 | 1/2003 | Dannecker et al. | |
| 6,511,669 B1 | 1/2003 | Garnier et al. | |
| 6,582,477 B1 | 6/2003 | Plos | |
| 6,613,313 B2 | 9/2003 | Kimura | |
| 6,770,271 B2 | 8/2004 | Mondet et al. | |
| 6,824,764 B2 * | 11/2004 | Devin-Baudoin et al. | 424/70.1 |
| 6,824,765 B2 * | 11/2004 | Gawtrey et al. | 424/70.1 |
| 6,846,333 B2 | 1/2005 | Legrand et al. | |
| 6,916,467 B2 | 7/2005 | Devin-Baudoin et al. | |
| 7,128,902 B2 * | 10/2006 | Legrand et al. | 424/70.122 |
| 7,135,167 B2 * | 11/2006 | Legrand et al. | 424/70.122 |
| 7,138,109 B2 * | 11/2006 | Devin-Baudoin et al. | 424/62 |
| 7,195,755 B2 * | 3/2007 | Nguyen et al. | 424/70.2 |
| 7,220,408 B2 * | 5/2007 | Decoster et al. | 424/70.12 |
| 7,223,385 B2 * | 5/2007 | Gawtrey et al. | 424/70.12 |
| 2002/0006389 A1 | 1/2002 | Restle et al. | |
| 2002/0187117 A1 | 12/2002 | Devin-Baudoin et al. | |

FOREIGN PATENT DOCUMENTS

| | | |
|---|---|---|
| EP | 0 122 324 | 10/1984 |
| EP | 0 337 354 | 10/1989 |
| EP | 0 342 834 | 11/1989 |
| EP | 0 412 704 | 2/1991 |
| EP | 0 412 707 | 2/1991 |
| EP | 0 486 135 | 5/1992 |
| EP | 0 582 152 | 2/1994 |
| EP | 0 619 111 | 10/1994 |
| EP | 0 646 572 | 4/1995 |
| EP | 0 227 994 | 7/1997 |
| EP | 0 890 355 | 1/1999 |
| GB | 0 839 805 | 6/1960 |
| GB | 0 922 457 | 4/1963 |
| GB | 1 021 400 | 3/1966 |
| GB | 1 026 978 | 4/1966 |
| GB | 1 153 196 | 5/1969 |
| GB | 1 486 576 | 9/1977 |
| GB | 1 546 809 | 5/1979 |
| GB | 2 058 103 | 4/1981 |
| GB | 2 141 454 | 12/1984 |
| GB | 2 165 550 | 4/1986 |
| WO | WO 93/23446 | 11/1993 |
| WO | WO 94/07844 | 4/1994 |
| WO | WO 94/10131 | 5/1994 |
| WO | WO 95/00578 | 1/1995 |
| WO | WO 95/01772 | 1/1995 |
| WO | WO 95/15144 | 6/1995 |
| WO | WO 95/16665 | 6/1995 |

OTHER PUBLICATIONS

Charles Todd et al., "Volatile Silicone Fluids for Cosmetic Formulations," Cosmetics and Toiletries, vol. 91, Jan. 1976, pp. 29-32.

"Encyclopedia of Chemical Technology", Kirk-Othmer, Third Edition, 1982, vol. 15, pp. 439-458.

"Encyclopedia of Chemical Technology", Kirk-Othmer, Third Edition, 1982, vol. 22, pp. 332-433.

"Encyclopedia of Chemical Technology", Kirk-Othmer, Third Edition, 1982, vol. 3, pp. 896-900.

"Industrial Gums—Polysaccharides and their Derivatives", edited by Roy L. Whistler, Second Edition, Academic Press.

"Polymers in Nature", E.A. MacGregor & C.T. Greenwood, John Wiley & Sons, Chapter 6, pp. 240-328, 1980.

Copending U.S. Appl. No. 10/290,149, filed Nov. 8, 2002.
Copending U.S. Appl. No. 10/290,159, filed Nov. 8, 2002.
Copending U.S. Appl. No. 10/290,189, filed Nov. 8, 2002.
Copending U.S. Appl. No. 10/290,192, filed Nov. 8, 2002.
Copending U.S. Appl. No. 10/290,226, filed Nov. 8, 2002.
Copending U.S. Appl. No. 10/290,342, filed Nov. 8, 2002.
Copending U.S. Appl. No. 10/290,343, filed Nov. 8, 2002.
Copending U.S. Appl. No. 10/290,345, filed Nov. 8, 2002.
Copending U.S. Appl. No. 10/290,348, filed Nov. 8, 2002.
Copending U.S. Appl. No. 11/158,014, filed Jun. 22, 2005.
English language Derwent Abstract of DE 42 29 922, Mar. 10, 1994.
English language Derwent Abstract of DE 44 02 929, Jun. 22, 1995.
English language Derwent Abstract of DE 44 20 736, Aug. 10, 1995.

English language Derwent Abstract of DE 44 24 530, Jan. 18, 1996.
English language Derwent Abstract of DE 44 24 533, Jan. 18, 1996.
English language Derwent Abstract of DE 197 54 053, filed Jun. 10, 1999.
English language Derwent Abstract of EP 0 080 976, Jun. 8, 1983.
English language Derwent Abstract of EP 0 225 261, Jun. 10, 1987.
English language Derwent Abstract of EP 0 368 763, May 16, 1990.
English language Derwent Abstract of EP 0 765 655, Apr. 2, 1987.
English language Derwent Abstract of FR 2 679 448, Jan. 29, 1993.
English language Derwent Abstract of FR 2 679 558, Jan. 29, 1993.
English language Patent Abstract of Japan of JP 2001-10935, Jan. 16, 2001.
English language Derwent Abstract of JP 2001-10936, Jan. 16, 2001.
English language Derwent Abstract of JP 2-250814, Oct. 8, 1990.
English language Derwent Abstract of JP 4-154713, May 27, 1992.
English language Derwent Abstract of JP 8-157340, Jun. 18, 1996.
English language Derwent Abstract of JP 9-151120, Jun. 10, 1997.
English language JAPIO Abstract of JP 2-019576, Jan. 23, 1990.
English language JAPIO Abstract of JP 9-110659, Apr. 28, 1997.
French Search Report for FR 0 114 468, dated Aug. 8, 2002, related to U.S. Appl. No. 10/290,341.
French Search Report for FR 0 114 469, dated Aug. 22, 2002, related to U.S. Appl. No. 10/290,345.
French Search Report for FR 0 114 470, dated Sep. 18, 2002, related to U.S. Appl. No. 10/290,208.
French Search Report for FR 0 114 472, dated Aug. 30, 2002, related to U.S. Appl. No. 10/290,342.
French Search Report for FR 0 114 473, dated Sep. 16, 2002, related to U.S. Appl. No. 10/290,192.
French Search Report for FR 0 114 474, dated Aug. 8, 2002, related to U.S. Appl. No. 10/290,372.
French Search Report for FR 0 114 476, dated Sep. 20, 2002, related to U.S. Appl. No. 10/290,409.
French Search Report for FR 0 114 477, dated Sep. 20, 2002, related to U.S. Appl. No. 10/290,409.
French Search Report for FR 0 114 478, dated Sep. 18, 2002, related to U.S. Appl. No. 10/290,189.
French Search Report for FR 0 114 479, dated Sep. 16, 2002, related to U.S. Appl. No. 10/290,148.
French Search Report for FR 0 114 480, dated Aug. 9, 2002, related to U.S. Appl. No. 10/290,226.
French Search Report for FR 0 114 481, dated Sep. 4, 2002, related to U.S. Appl. No. 10/290,159.
French Search Report for FR 0 114 482, dated Aug. 28, 2002, related to U.S. Appl. No. 10/290,226.
French Search Report for FR 0 114 484, dated Sep. 4, 2002, related to U.S. Appl. No. 10/290,149.
French Search Report for FR 0 114 485, dated Aug. 29, 2002, related to U.S. Appl. No. 10/290,343.
French Search Report for FR 0 114 486, dated Sep. 23, 2002, related to U.S. Appl. No. 10/290,348.
Office Action in co-pending U.S. Appl. No. 10/290,149, dated Apr. 30, 2004 (Ex. Elhilo).
Office Action in co-pending U.S. Appl. No. 10/290,149, dated Nov. 4, 2004 (Ex. Elhilo).
Office Action in co-pending U.S. Appl. No. 10/290,159, dated Dec. 27, 2004 (Ex. Elhilo).
Office Action in co-pending U.S. Appl. No. 10/290,159, dated May 3, 2004 (Ex. Elhilo).
Office Action in co-pending U.S. Appl. No. 10/290,189, dated Feb. 16, 2006 (Ex. Venkat).
Office Action in co-pending U.S. Appl. No. 10/290,192, dated Jun. 23, 2006 (Ex. Venkat).
Office Action in co-pending U.S. Appl. No. 10/290,192, dated Jan. 11, 2006 (Ex. Venkat).
Office Action in co-pending U.S. Appl. No. 10/290,208, dated Jan. 11, 2006 (Ex. Venkat).
Office Action in co-pending U.S. Appl. No. 10/290,226, dated Apr. 19, 2006 (Ex. Venkat).
Office Action in co-pending U.S. Appl. No. 10/290,341, dated Jan. 11, 2006 (Ex. Venkat).
Office Action in co-pending U.S. Appl. No. 10/290,342, dated Jan. 25, 2006 (Ex. Venkat).
Office Action in co-pending U.S. Appl. No. 10/290,342, dated Jul. 10, 2006 (Ex. Venkat).
Office Action in co-pending U.S. Appl. No. 10/290,343, dated Jan. 25, 2006 (Ex. Venkat).
Office Action in co-pending U.S. Appl. No. 10/290,345, dated Feb. 9, 2006 (Ex. Venkat).
Office Action in co-pending U.S. Appl. No. 10/290,348, dated Apr. 19, 2006 (Ex. Venkat).
Office Action in co-pending U.S. Appl. No. 10/290,372, dated Jan. 10, 2006 (Ex. Venkat).
Porter, M.R., Handbook of Surfactants 116-178 (Blackie & Son 1991).

* cited by examiner

COSMETIC COMPOSITIONS CONTAINING A PARTICULAR AMINOSILICONE AND A CONDITIONER, AND USES THEREOF

This is a divisional application of application Ser. No. 10/290,409, filed Nov. 8, 2002, now U.S. Pat. No. 7,223,385 which claims the benefit of French Patent Application No. 01 14476, filed Nov. 8, 2001, and French Patent Application No. 01 14477, filed Nov. 8, 2001, all of which are incorporated herein by reference.

Disclosed herein is a novel cosmetic composition comprising, in a cosmetically acceptable medium, at least one particular aminosilicone and at least one conditioner, as well as uses of this aminosilicone.

It is well known that hair that has been sensitized (i.e. damaged and/or embrittled) to varying degrees by the action of atmospheric agents or by the action of mechanical or chemical treatments, such as dyeing, bleaching and/or permanent-waving, may often be difficult to disentangle and to style, and may lack softness.

It has already been recommended, in compositions for washing or caring for keratin materials such as the hair, to use conditioners, such as cationic polymers or silicones, to facilitate the disentangling of the hair and to impart softness and suppleness thereto. However, at least one of the cosmetic advantages mentioned above can unfortunately also be accompanied, on dried hair, by certain cosmetic effects considered undesirable, namely a lank effect on the hairstyle (lack of lightness of the hair) and a lack of smoothness (hair not uniform from the root to the end).

In addition, the use of aminosilicones for this purpose can have various drawbacks. On account of their strong affinity for hair, some of these silicones can become deposited in considerable amount during repeated use, and can lead to adverse effects such as an unpleasant, laden (charged or loaded) feel, stiffening of the hair and adhesion between fibres, affecting the styling. These drawbacks can be accentuated in the case of fine hair, which lacks liveliness and volume.

In summary, it is found that the current cosmetic compositions containing conditioners are not always entirely satisfactory.

The inventors have now discovered that the combination of a particular aminosilicone with at least one conditioner makes it possible to overcome at least one of these drawbacks.

The inventors have now found that a composition comprising at least one aminosilicone as defined below and at least one conditioner, makes it possible to limit or even eliminate at least one of the lack of sheen, smoothness and softness of the hair, while at the same time retaining at least one of the other advantageous cosmetic properties associated with compositions containing a silicone.

The composition disclosed herein can also afford at least one improved cosmetic property (such as lightness, disentangling, volume, smoothness and sheen) and, what is more, the effects can be persistent and remanent.

The inventors have now found that the remanence of at least one cosmetic property (such as the conditioning effects) can be improved by the presence of the at least one aminosilicone defined below.

The compositions disclosed herein when applied to the skin, such as in the form of a bubble bath or shower gel, can afford an improvement in the softness of the skin.

The compositions disclosed herein can also promote the deposition of conditioners onto keratin materials.

Thus, novel cosmetic compositions are now proposed, comprising, in a cosmetically acceptable medium, at least one aminosilicone as defined below and at least one conditioner.

Another new embodiment relates to the inclusion of at least one aminosilicone as defined below, in, or for the manufacture of, a cosmetic composition comprising at least one conditioner.

Another new embodiment relates to a composition comprising at least one aminosilicone as defined below and at least one conditioner, as well as methods, for conditioning a keratin material.

Another new embodiment relates to a composition comprising at least one aminosilicone as defined below and at least one conditioner, as well as methods, for improving the lightness, softness, sheen and/or disentangling, and/or facilitating the styling of keratin materials.

Another new embodiment relates to a composition comprising at least one aminosilicone as defined below and at least one conditioner, as well as a method, for improving remanence of the conditioning effects with respect to shampooing.

Another new embodiment relates to the at least one aminosilicone as defined below, as well as methods, for improving remanence of the conditioning effects of a cosmetic composition with respect to shampooing.

Another new embodiment relates to a process to improve remanence of the conditioning effects of a cosmetic composition with respect to shampooing comprising including the at least one aminosilicone as defined below in the cosmetic composition.

Various illustrative new embodiments will now be described in detail. All the meanings and definitions of the compounds given below are valid for all embodiments.

In context, the term "keratin materials" means hair, eyelashes, eyebrows, skin, nails, mucous membranes or scalp.

The at least one aminosilicone is chosen from aminosilicones of formulae (I) and (II) below:

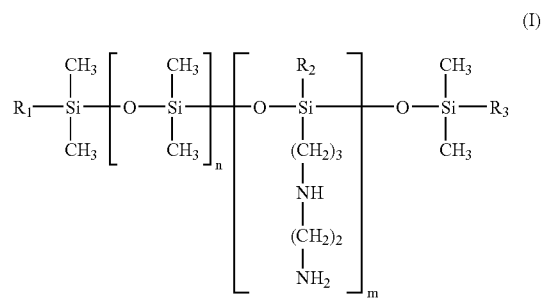

in which:

m and n are numbers such that the sum (n+m) ranges, for example, from 1 to 1000, such as from 50 to 250 and further such as from 100 to 200, n is a number ranging from 0 to 999, such as from 49 to 249 and further, such as from 125 to 175, and m is a number ranging from 1 to 1000, such as from 1 to 10 and further such as from 1 to 5;

$R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals.

In one embodiment, the alkoxy radical is a methoxy radical.

The hydroxyl/alkoxy molar ratio may range, for example, from 0.2:1 to 0.4:1 and further, for example, from 0.25:1 to 0.35:1, and even further, for example, is equal to 0.3:1.

The aminosilicone of formula (I) can have a weight-average molecular mass ranging, for example, from 2,000 to 1,000,000, and further, for example, from 3 500 to 200,000; and

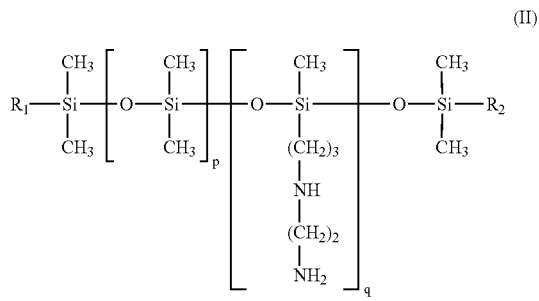

(II)

in which:

p and q are numbers such that the sum (p+q) ranges, for example, from 1 to 1 000, such as from 50 to 350 and further such as from 150 to 250, p is a number ranging from 0 to 999, and further, for example, from 49 to 349, and even further, for example, from 159 to 239; and q is a number ranging from 1 to 1,000, and further, for example, from 1 to 10 and even further, for example, from 1 to 5;

$R_1$, $R_2$, which may be identical or different, are chosen from hydroxyl and $C_1$-$C_4$ alkoxy radicals, wherein at least one of the radicals $R_1$ and $R_2$ is chosen from $C_1$-$C_4$ alkoxy radicals.

In one embodiment, the alkoxy radical is a methoxy radical.

The hydroxyl/alkoxy molar ratio may range, for example, from 1:0.8 to 1:1.1 and further, for example, from 1:0.9 to 1:1, and even further, for example, is equal to 1:0.95.

The aminosilicone of formula (II) may have a weight-average molecular mass ranging, for example, from 2,000 to 200,000, and further, for example, from 5 000 to 100,000, and even further, for example, from 10,000 to 50,000.

The weight-average molecular masses of these aminosilicones are measured by Gel Permeation Chromatography (GPC) at room temperature as polystyrene equivalent. The columns used are μ styragel columns. The eluent is THF, the flow rate is 1 ml/min. 200 μl of a solution containing 0.5% by weight of silicone in THF are injected. The detection is made by refractometry and UV-metry.

The commercial products corresponding to these aminosilicones of formula (I) or (II) may include in their composition at least one other aminosilicone whose structure is different from the formulae (I) and (II).

A product containing aminosilicones of formula (I) is proposed by the company Wacker under the name Belsil ADM 652®.

Products containing aminosilicones of formula (II) are proposed by the company Wacker under the names Fluid WR 1300®.

In one new embodiment, the at least one aminosilicone can be used in the form of an oil-in-water emulsion. The oil-in-water emulsion may comprise at least one surfactant. The at least one surfactant may be of any nature, such as cationic and/or nonionic.

The number-average particle size (i.e., the mean particle size) of the at least one aminosilicone in the emulsion is, for example, ranging from 3 to 500 nanometers. Such particle size is measured with a laser granulometer.

For example, the at least one aminosilicone of formula (II) in microemulsions having a mean particle size ranging, for example, from 5 to 60 nanometers and such as from 10 to 50 nanometers can be used.

Thus, the microemulsions of at least one aminosilicone of formula (II) sold under the name Finish CT 96 E® or SLM 28020® by the company Wacker may be used.

In one embodiment, the at least one aminosilicone chosen from formulae (I) and (II) is chosen such that the contact angle with water of hair treated with a composition comprising 2% AM (active materials) of the aminosilicone ranges, for example, from 90 to 180°, and such as from 90 to 130°. As used herein, a range "from x to y" includes within the range the endpoints x and y.

To measure the contact angle, the at least one aminosilicone is, for example, dissolved or dispersed in a solvent for the aminosilicone or for the aminosilicone emulsion (such as hexamethyldisiloxane or water depending on the hydrophilicity of the aminosilicone).

In another embodiment, the composition comprising at least one aminosilicone chosen from aminosilicones of formulae (I) and (II) is chosen such that the contact angle of hair treated with the composition ranges, for example, from 90 to 180° such as from 90 to 130°.

The measurement of the contact angle is based on the immersion of hair in distilled water. The measurement includes evaluating the force exerted by the water on the hair during its immersion in distilled water and during its removal. The forces thus measured are directly linked to the contact angle θ between the water and the surface of the hair. The hair is said to be hydrophilic when the angle θ ranges from 0 to less than 90°, and hydrophobic when this angle ranges from 90° to 180°.

The test is carried out with locks of natural hair that have been bleached under the same conditions and then washed.

Each 1 g lock is placed in a crystallizing dish 75 mm in diameter and then covered uniformly with 5 ml of the test formulation. The lock is thus left for 15 minutes at room temperature and then rinsed with distilled water for 30 seconds. The drained lock is left in the open air until it is completely dry.

For each evaluation, 10 hair strands that have undergone the same treatment are analysed. Each sample, attached to a precision microbalance, is immersed via its end in a container filled with distilled water. This DCA balance ("Dynamic Contact Angle Analyser"), from the company Cahn Instruments, allows the force (F) exerted by the water on the hair to be measured.

In parallel, the perimeter (P) of the hair is measured by means of observation by microscope.

The mean wettability force on 10 hair strands and the section of the analysed hairs make it possible to obtain the contact angle of the hair on the water, according to the formula:

$$F = P * \lceil lv * \cos\theta$$

where F is the wettability force expressed in newtons, P is the perimeter of the hair in meters, ⌈lv is the liquid/water vapour interface tension in $J/m^2$ and θ is the contact angle.

The product SLM 28020® from Wacker at 12% in water (i.e. 2% aminosilicone as active material) gives a contact angle of 93° according to the test indicated above.

The product Belsil ADM 652 from Wacker at 2% in hexamethyldisiloxane (i.e. 2% aminosilicone as active material) gives a contact angle of 111° according to the test indicated above.

The at least one aminosilicone is present in an amount ranging, for example, from 0.01% to 20% by weight relative to the total weight of the composition. Further, for example, this amount ranges from 0.1% to 15% by weight and even further, for example, from 0.5% to 10% by weight, relative to the total weight of the composition.

As used herein, the term "conditioner" means any agent whose function is to improve at least one cosmetic property of a keratin material such as hair, for example, the softness, smoothness, disentangling, feel and static electricity.

The at least one conditioner may be soluble or insoluble in water.

The at least one conditioner is, for example, chosen from synthetic oils such as polyolefins, mineral oils, plant oils, fluoro oils and perfluoro oils, natural and synthetic waxes, compounds of ceramide type, carboxylic acid esters, silicones other than those of formula (I) or (II), anionic polymers, nonionic polymers, cationic polymers, amphoteric polymers, cationic proteins, cationic protein hydrolysates and cationic surfactants, usually used in cosmetic and/or dermatological compositions.

The insoluble conditioner may be solid, liquid or pasty at room temperature (25° C.) and at atmospheric pressure, and may, for example, be in the form of oils, waxes, resins or gums.

The insoluble conditioner can, for example, be dispersed in the composition in the form of particles having a number-average size ranging, for example, from 2 nanometers to 100 microns and further, for example, from 30 nanometers to 20 microns. The number-average size of insoluble conditioner particles is measured with a granulometer.

The water-insoluble conditioners are insoluble in water at a concentration of greater than or equal to 0.1% by weight in water at 25° C., i.e. they do not form a macroscopically isotropic transparent solution under these conditions.

The synthetic oils are, for example, polyolefins, such as poly-α-olefins and further such as:

poly-α-olefins of hydrogenated and non-hydrogenated polybutene type, and even further such as hydrogenated and non-hydrogenated polyisobutenes.

Isobutylene oligomers with a molecular weight of less than 1000 and mixtures thereof with polyisobutylenes with a molecular weight of greater than 1000, and such as from 1000 to 15,000, can, for example, be used.

Among the poly-α-olefins, which can be used, mention may be made, for example, of the products sold under the name Permethyl® 99 A, 101 A, 102 A, 104 A (n=16) and 106 A (n=38) by the company Presperse Inc., or the products sold under the name Arlamol® HD (n=3) by the company ICI (n denoting the degree of polymerization), and poly-α-olefins of hydrogenated and non-hydrogenated polydecene type.

Such products are sold, for example, under the names Ethylflo® by the company Ethyl Corp., and Arlamol® PAO by the company ICI.

The animal and plant oils are, for example, chosen from sunflower oil, corn oil, soybean oil, avocado oil, jojoba oil, marrow oil, grapeseed oil, sesame oil, hazelnut oil, fish oils, glyceryl tricaprocaprylate, and plant and animal oils of formula $R_9COOR_{10}$, in which $R_9$ is chosen from higher fatty acid residues containing from 7 to 29 carbon atoms and $R_{10}$ is chosen from linear and branched hydrocarbon-based chains containing from 3 to 30 carbon atoms, such as alkyl and alkenyl, for example, purcellin oil and liquid jojoba wax.

It is also possible to use natural or synthetic essential oils such as eucalyptus oil, lavendin oil, lavender oil, vetiver oil, *Litsea cubeba* oil, lemon oil, sandalwood oil, rosemary oil, camomile oil, savory oil, nutmeg oil, cinnamon oil, hyssop oil, caraway oil, orange oil, geraniol oil, cade oil and bergamot oil.

The waxes are natural (animal or plant) or synthetic substances that are solid at room temperature (20°-25° C.). They are insoluble in water, soluble in oils and are capable of forming a water-repellent film.

Among the waxes, mention may be made, for example, of those disclosed in P. D. Dorgan, Drug and Cosmetic Industry, December 1983, pp. 30-33.

The waxes are chosen, for example, from carnauba wax, candelilla wax, alfalfa wax, paraffin wax, ozokerite, plant waxes such as olive tree wax, rice wax, hydrogenated jojoba wax and absolute waxes of flowers such as the essential wax of blackcurrant flower sold by the company Bertin (France), animal waxes such as beeswaxes, and modified beeswaxes (cerabellina). Other waxes or waxy starting materials, which can be used, include, for example, marine waxes such as the product sold by the company Sophim under the reference M82, and polyethylene waxes and polyolefins in general.

The compounds of ceramide type are chosen, for example, from natural and synthetic ceramides, glycoceramides, pseudoceramides, and neoceramides.

Compounds of ceramide type are described, for example, in patent applications DE 4,424,530, DE 4,424,533, DE 4,402,929, DE 4,420,736, WO 95/23807, WO 94/07844, EP-A-0,646,572, WO 95/16665, FR-2,673,179, EP-A-0,227,994, WO 94/07844, WO 94/24097 and WO 94/10131, the teachings of which are incorporated herein by reference.

Compounds of ceramide type include, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and such as N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine, and mixtures of these compounds.

The fluoro oils are, for example, the perfluoropolyethers described, for example, in patent application EP-A-486 135 and the fluorohydrocarbon compounds described, for example, in patent application WO 93/11103.The teaching of these two patent applications is incorporated herein by reference.

The term "fluorohydrocarbon compounds" means compounds whose chemical structure contains a carbon skeleton in which at least one hydrogen atom has been replaced with a fluorine atom.

The fluoro oils can also be fluorocarbons such as fluoroamines, for example perfluorotributylamine, fluorohydrocarbons, for example perfluorodecahydronaphthalene, fluoro esters and fluoro ethers.

The perfluoropolyethers are sold, for example, under the trade names Fomblin by the company Montefluos and Krytox by the company Du Pont.

Among the fluorohydrocarbon compounds, mention may also be made, for example, of fluorine-containing fatty acid esters such as the product sold under the name Nofable FO by the company Nippon Oil.

The fatty alcohols may be chosen from linear and branched $C_8$-$C_{22}$ fatty alcohols, optionally oxyalkylenated with 1 to 15 mol of alkylene oxide or polyglycerolated with 1 to 6 mol of glycerol. The alkylene oxide is chosen, for example, from ethylene oxide and propylene oxide.

The carboxylic acid esters are chosen, for example, from mono-, di-, tri- and tetracarboxylic esters.

The monocarboxylic acid esters are chosen, for example, from linear and branched, saturated and unsaturated $C_1$-$C_{26}$ aliphatic acid monoesters of linear and branched, saturated and unsaturated, $C_1$-$C_{26}$ aliphatic alcohols, the total carbon number of these esters being greater than or equal to 10.

Among the monoesters, mention may be made, for example, of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl and 2-octyldodecyl myristate, hexyl stearate, butyl stearate, isobutyl stearate; dioctyl malate, hexyl laurate, and 2-hexyldecyl laurate.

$C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra- or pentahydroxy alcohols can also be used.

Mention may be made, for example, of: diethyl sebacate; diisopropyl sebacate; diisopropyl adipate; di-n-propyl adipate; dioctyl adipate; diisostearyl adipate; dioctyl maleate; glyceryl undecylenate; octyldodecylstearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; and trioleyl citrate.

Among the esters mentioned above, mention may be made, for example, of ethyl and isopropyl palmitates, 2-ethylhexyl palmitate, 2-octyldecyl palmitate, alkyl myristates such as isopropyl, butyl, cetyl and 2-octyldodecyl myristate, hexyl stearate, butyl stearate, isobutyl stearate; dioctyl malate, hexyl laurate, 2-hexyldecyl laurate, isononyl isononanoate and cetyl octanoate.

The silicones other than those of formula (I) or (II) are chosen, for example, from polyorganosiloxanes that can be insoluble in the composition and may be in the form of oils, waxes, resins or gums.

The organopolysiloxanes are defined in greater detail in Walter Noll's "Chemistry and Technology of Silicones" (1968) Academic Press. They can be volatile or non-volatile.

The volatile organopolysiloxanes are, for example, chosen from those having a boiling point ranging from 60° C. to 260° C., and further, for example, are chosen from:

(i) cyclic silicones comprising from 3 to 7 and such as 4 to 5 silicon atoms. These cyclic silicones are, for example, octamethylcyclotetrasiloxane sold, for example, under the name "Volatile Silicone 7207" by Union Carbide or "Silbione 70045 V 2" by Rhodia Chimie, decamethylcyclopentasiloxane sold under the name "Volatile Silicone 7158" by Union Carbide, and "Silbione 70045 V 5" by Rhodia Chimie, and mixtures thereof.

Mention may also be made, for example, of cyclocopolymers of the dimethylsiloxanes/methylalkylsiloxane type, such as "Volatile Silicone FZ 3109" sold by the company Union Carbide, with the chemical structure:

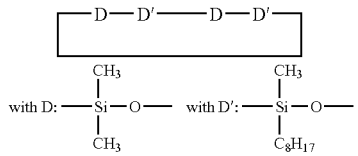

Mention may also be made of mixtures of cyclic silicones with organosilicone compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile silicones comprising from 2 to 9 silicon atoms and having a viscosity of less than or equal to $5 \times 10^{-6}$ m²/s at 25° C. An example is the decamethyltetrasiloxane sold, for example, under the name "SH 200" by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile silicones, and, for example, polyalkylsiloxanes, polyarylsiloxanes, polyalkylarylsiloxanes, silicone gums and resins, polyorganosiloxanes modified with organofunctional groups, and mixtures thereof may also be used.

These silicones are further, for example, chosen from polyalkylsiloxanes, among which mention may be made, for example, of polydimethylsiloxanes comprising trimethylsilyl end groups having a viscosity of from $5 \times 10^{-6}$ to 2.5 m²/s at 25° C. and such as from $1 \times 10^{-5}$ to 1 m²/s.

The viscosity of the silicones is measured at 25° C. according to ASTM standard 445 Appendix C.

Among these polyalkylsiloxanes, mention may be made, in a non-limiting manner, of the following commercial products:

the Silbione® oils of the 47 and 70,047 series or the Mirasil® oils sold by Rhodia Chimie, such as the oil 70 047 V 500,000;

the oils of the Mirasil series sold by the company Rhodia Chimie;

the oils of the 200 series from the company Dow Corning, such as DC200 with a viscosity of 60 000 cSt (mm²/s); and the Viscasil® oils from General Electric and certain oils of the SF series (SF 96, SF 18) from General Electric.

Mention may also be made, for example, of polydimethylsiloxanes comprising dimethylsilanol end groups (Dimethiconol according to the CTFA name) such as the oils of the 48 series from the company Rhodia Chimie.

In this category of polyalkylsiloxanes, mention may also be made, for example, of the products sold under the names "Abil® Wax 9800 and 9801" by the company Goldschmidt, which are poly($C_1$-$C_{20}$)alkylsiloxanes.

The polyalkylarylsiloxanes are chosen, for example, from linear and branched polydimethylmethylphenylsiloxanes and polydimethyldiphenylsiloxanes with a viscosity of from $1 \times 10^{-5}$ to $5 \times 10^{-2}$ m$^2$/s at 25° C.

Among these polyalkylarylsiloxanes, mention may be made, for example, of the products sold under the following names:

- the Silbione oils of the 70,641 series from Rhodia Chimie;
- the oils of the Rhodorsil 70,633 and 763 series from Rhodia Chimie;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000; and
- certain oils of the SF series from General Electric, such as SF 1023, SF 1154, SF 1250 and SF 1265.

The silicone gums, are, for example, chosen from polydiorganosiloxanes having the number-average molecular masses ranging from 200,000 to 1,000,000, used alone or as a mixture in a solvent. This solvent can, for example, be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, and mixtures thereof.

Mention may also be made, for example, of the following polymers:
- polydimethylsiloxane,
- polydimethylsiloxane/methylvinylsiloxane gums,
- polydimethylsiloxane/diphenylsiloxane,
- polydimethylsiloxane/phenylmethylsiloxane, and
- polydimethylsiloxane/diphenylsiloxane/methylvinylsiloxane.

Products, which can be used, for example, are mixtures such as:
- mixtures formed from a polydimethylsiloxane hydroxylated at the end of the chain (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;
- mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500,000, dissolved in the oil SF 1202 Silicone Fluid corresponding to decamethylcyclopentasiloxane; and
- mixtures of two PDMSs of different viscosities, for example, of a PDMS gum and a PDMS oil, such as the product SF 1236 from the company General Electric. The product SF 1236 is a mixture of an SE 30 gum defined above, having a viscosity of 20 m2/s, and an SF 96 oil, with a viscosity of $5 \times 10^{-6}$ m$^2$/s. This product, for example, contains 15% SE 30 gum and 85% SF 96 oil.

The organopolysiloxane resins that can be used are crosslinked siloxane systems comprising at least one of the following units:

$R_2SiO_{2/2}$, $R_3SiO_{1/2}$, $RSiO_{3/2}$ and $SiO_{4/2}$ wherein R is chosen from hydrocarbon-based groups comprising from 1 to 16 carbon atoms and phenyl groups. Among these products, examples include the ones in which R is chosen from $C_1$-$C_4$ lower alkyl radicals, such as methyl, and a phenyl radical.

Among these resins, mention may be made, for example, of the product sold under the name "Dow Corning 593" or those sold under the names "Silicone Fluid SS 4230 and SS 4267" by the company General Electric, which are silicones of dimethyl/trimethyl siloxane structure.

Mention may also be made, for example, of the trimethyl siloxysilicate type resins sold, for example, under the names X22-4914, X21-5034 and X21-5037 by the company Shin-Etsu.

The organomodified silicones are silicones as defined above and containing in their structure at least one organofunctional group attached via a hydrocarbon-based radical.

Among the organomodified silicones other than those of formula (I) or (II), mention may be made, for example, of polyorganosiloxanes comprising at least one group chosen from:

- polyethylenoxy and polypropylenoxy groups optionally containing $C_6$-$C_{24}$ alkyl groups, such as the products known as dimethicone copolyol sold by the company Dow Corning under the name DC 1248 and the ($C_{12}$) alkylmethicone copolyol sold by the company Dow Corning under the name Q2 5200;
- substituted and unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, chosen from $C_1$-$C_4$ aminoalkyl groups;
- thiol groups such as the products sold under the names "GP 72 A" and "GP 71" from Genesee;
- alkoxylated groups such as the product sold under the name "Silicone Copolymer F-755" by SWS Silicones and Abil Wax 24,282,434 and 2440 by the company Goldschmidt;
- hydroxylated groups such as the polyorganosiloxanes containing a hydroxyalkyl function, described in French patent application FR-A-85/16334;
- acyloxyalkyl groups such as, for example, the polyorganosiloxanes described in U.S. Pat. No. 4,957,732;
- anionic groups of carboxylic type, such as in the products described in patent EP 186 507 from the company Chisso Corporation, and anionic groups of alkylcarboxylic type, such as those present in the product X-22-3701 E from the company Shin-Etsu; 2-hydroxyalkyl sulphonate; 2-hydroxyalkyl thiosulphate such as the products sold by the company Goldschmidt under the names "Abil S201" and "Abil S255";
- hydroxyacylamino groups, such as the polyorganosiloxanes described in patent application EP 342 834. Mention may be made, for example, of the product Q2-8413 from the company Dow Corning.

The silicones, which can also be used, comprise a polysiloxane portion and a portion comprising a non-silicone organic chain, one of the two portions constituting the main chain of the polymer, the other being grafted onto said main chain. These polymers are described, for example, in patent applications EP-A-412 704, EP-A-412 707, EP-A-640 105, WO 95/00578, EP-A-582 152 and WO 93/23009 and U.S. Pat. Nos. 4,693,935, 4,728,571 and 4,972,037. These polymers are, for example, anionic or nonionic.

Such polymers are, for example, copolymers that can be obtained by radical polymerization starting with a monomer mixture comprising:

a) 50 to 90% by weight of tert-butyl acrylate;

b) 0 to 40% by weight of acrylic acid;

c) 5 to 40% by weight of silicone macromer of the formula (IIa):

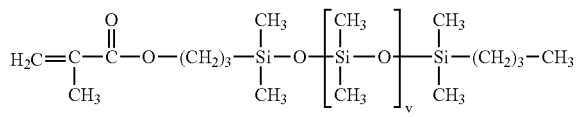

(IIa)

wherein v is a number ranging from 5 to 700; and the weight percentage is calculated relative to the total weight of the monomers.

Other examples of the grafted silicone polymers include, for example, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl (meth) acrylate type.

All of the silicones can also be used in the form of emulsions, nanoemulsions or microemulsions.

The silicones, which can be used, include, for example:

non-volatile silicones chosen from polyalkylsiloxanes comprising trimethylsilyl end groups, such as oils having a viscosity ranging from 0.2 to 2.5 m²/s at 25° C., such as the oils of the DC200 series from Dow Corning, for example, oils with a viscosity of 60 000 cSt, of the Silbione 70047 and 47 series and further, for example, the oil 70 047 V 500 000, which are sold by the company Rhodia Chimie, polyalkylsiloxanes comprising dimethylsilanol end groups, such as dimethiconols, and polyalkylarylsiloxanes such as the oil Silbione 70641 V 200 sold by the company Rhodia Chimie;

the polyorganosiloxane resin sold under the name Dow Corning 593; and polysiloxanes containing amine groups, such as amodimethicones other than those of formula (I) and trimethylsilylamodimethicones.

The conditioners that are mentioned below may be water-soluble, for example, anionic polymers, nonionic polymers, cationic polymers, amphoteric polymers, cationic proteins, cationic protein hydrolysates and cationic surfactants, and also mixtures of these various compounds.

The anionic polymers generally used are polymers comprising at least one group derived from carboxylic acid, sulphonic acid or phosphoric acid and such as those having a weight-average molecular weight ranging approximately from 500 to 5 000 000, determined, for example, by gel permeation chromatography.

The anionic polymers may be, for example, chosen from:

1) polymers comprising carboxylic units derived from unsaturated mono- or dicarboxylic acid monomers such as those corresponding to the formula (III):

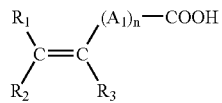

(III)

in which n is an integer ranging from 0 to 10, $A_1$ is a methylene group, optionally connected to the carbon atom of the unsaturated group, or to the neighbouring methylene group when n is greater than 1, via a hetero atom such as oxygen or sulphur, $R_1$ is chosen from a hydrogen atom and phenyl and benzyl groups, $R_2$ is chosen from a hydrogen atom and lower alkyl and carboxyl groups, $R_3$ is chosen from a hydrogen atom, lower alkyl groups and —$CH_2$—COOH, phenyl and benzyl groups;

In the above-mentioned formula, the lower alkyl radicals are chosen, for example, from alkyl radicals comprising from 1 to 4 carbon atoms and such as methyl and ethyl.

The anionic film-forming polymers containing carboxylic groups may, for example, be chosen from:

A) acrylic and methacrylic acid homo- and copolymers, and salts thereof, such as the products sold under the names Versicol E or K by the company Ciba and Ultrahold by the company BASF. The copolymers of acrylic acid and of acrylamide sold in the form of their sodium salt under the names Reten 421, 423 or 425 by the company Hercules, the sodium salts of polyhydroxycarboxylic acids.

B) copolymers of acrylic and methacrylic acids with a monoethylenic monomer such as ethylene, styrene, vinyl esters, acrylic and methacrylic acid esters, optionally grafted onto a polyalkylene glycol such as polyethylene glycol and optionally crosslinked. Such polymers are described, for example, in French Patent No. 1,222,944 and German patent application 2,330,956, the copolymers of this type containing an optionally N-alkylated and/or hydroxyalkylated acrylamide unit in their chain as described, for example, in Luxembourg patent applications 75370 and 75371 or sold under the name Quadramer by the company American Cyanamid. Mention may also be made, for example, of copolymers of acrylic acid and of $C_1$-$C_4$ alkyl methacrylate and terpolymers of vinylpyrrolidone, of acrylic acid and of methacrylate of $C_1$-$C_{20}$ alkyl, for example, lauryl, such as the product sold by the company ISP under the name Acrylidone LM and methacrylic acid/ethyl acrylate/tert-butyl acrylate terpolymers such as the product sold under the name Luvimer 100 P by the company BASF.

C) copolymers derived from crotonic acid such as those containing vinyl acetate or propionate units in their chain and, for example, other monomers such as allylic esters and methallylic esters, vinyl ether and vinyl ester of an acid chosen from linear branched saturated carboxylic acids with a long hydrocarbon chain such as those containing at least 5 carbon atoms, it being possible for these polymers optionally to be grafted and crosslinked, or vinyl, allylic and methallylic esters of an α- or β-cyclic carboxylic acid. Such polymers are described, inter alia, in French Patent Nos. 1,222,944, 1,580,545, 2,265,782, 2,265,781, 1,564, 110 and 2,439,798.Commercial products falling into this class include the resins 28-29-30, 26-13-14 and 28-13-10 sold by the company National Starch.

D) copolymers derived from $C_4$-$C_8$ monounsaturated carboxylic acids or anhydrides chosen from:

copolymers comprising (i) at least one unit derived from maleic, fumaric and itaconic acids and anhydrides and (ii) at least one monomeric unit derived from vinyl esters, vinyl ethers, vinyl halides, phenylvinyl derivatives, acrylic acids and esters thereof, the anhydride functions of these copolymers optionallybeing monoesterified or monoamidated. Such polymers are described, for example, in U.S. Pat. Nos. 2,047,398, 2,723,248 and 2,102,113 and GB patent 839 805 and such as those sold under the names Gantrez AN or ES by the company ISP.

copolymers comprising (i) at least one unit chosen from maleic, citraconic and itaconic anhydrides and (ii) at least one monomeric unit chosen from allylic and methallylic estersoptionally containing at least one group chosen from acrylamide, methacrylamide, α-olefin, acrylic and methacrylic ester, acrylic and methacrylic acid and vinylpyrrolidone groups in their chain, the anhydride functions of these copolymers optionally being monoesterified or monoamidated.

These polymers are described, for example, in French patents 2 350 384 and 2,357,241.

E) polyacrylamides containing carboxylate groups.

2) The polymers comprising sulphonic groups are, for example, polymers containing vinylsulphonic, styrenesulphonic, naphthalenesulphonic or acrylamidoalkylsulphonic units.

These polymers can be chosen, for example, from:

polyvinylsulphonic acid salts having a weight-average molecular weight ranging, for example, from 1000 to 100 000, as well as the copolymers with an unsaturated comonomer such as acrylic or methacrylic acids and their esters, as well as acrylamide and its derivatives, vinyl ethers and vinylpyrrolidone;

polystyrenesulphonic acid salts, such as the sodium salts thereof, having a weight-average molecular weight ranging, for example, from 500,000 to 100,000, which are sold under the names Flexan 500 and Flexan 130 by National Starch. These compounds are described in French Patent No. FR 2 198 719;

polyacrylamidosulphonic acid salts, those mentioned in U.S. Pat. No. 4,128,631 and, for example, polyacrylamidoethylpropanesulphonic acid sold under the name Cosmedia Polymer HSP 1180 by Cognis.

The anionic film-forming polymers may be, for example, chosen from acrylic acid copolymers, such as the acrylic acid/ethyl acrylate/N-tert-butylacrylamide terpolymer sold under the name Ultrahold Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymer sold under the name Gantrez ES 425 by the company ISP, the copolymers of methacrylic acid and methyl methacrylate sold under the name Eudragit L by the company Rohm Pharma, the copolymer of methacrylic acid and ethyl acrylate sold under the name Luvimer MAEX or MAE by the company BASF and the vinyl acetate/crotonic acid copolymer sold under the name Luviset CA 66 by the company BASF and the vinyl acetate/crotonic acid copolymer grafted with polyethylene glycol under the name Aristoflex A by the company BASF.

The anionic film-forming polymers may be also chosen, for example, from the methyl vinyl ether/monoesterified maleic anhydride copolymer sold under the name Gantrez ES 425 by the company ISP, the acrylic acid/ethyl acrylate/N-tert-butylacrylamide terpolymer sold under the name Ultrahold Strong by the company BASF, the copolymers of methacrylic acid and methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymer of methacrylic acid and ethyl acrylate sold under the name Luvimer MAEX or MAE by the company BASF and the vinylpyrrolidone/acrylic acid/lauryl methacrylate terpolymer sold under the name Acrylidone LM by the company ISP.

The amphoteric polymers may be chosen from polymers containing units K and M distributed randomly in the polymer chain, in which K is a unit derived from a monomer comprising at least one basic nitrogen atom and M is a unit derived from an acidic monomer comprising at least one group chosen from carboxylic and sulphonic groups, or K and M may be chosen from groups derived from carboxybetaine or sulphobetaine zwitterionic monomers.

K and M can also be chosen from cationic polymer chains comprising at least one amine group chosen from primary, secondary, tertiary and quaternary amine groups, in which at least one of the amine groups bears a carboxylic or sulphonic group connected via a hydrocarbon radical, or K and M can form part of a chain of a polymer comprising an α,β-dicarboxylic ethylene unit in which one of the carboxylic groups has been made to react with a polyamine comprising at least one amine group chosen from primary and secondary amine groups.

The amphoteric polymers corresponding to the definition given above, for example, are chosen from the following polymers:

(1) polymers resulting from the copolymerization of at least one monomer derived from a vinyl compound bearing a carboxylic group such as acrylic acid, methacrylic acid, maleic acid, and α-chloroacrylic acid, and at least one basic monomer derived from a substituted vinyl compound comprising at least one basic atom, such as dialkylaminoalkyl methacrylates and acrylates, dialkylaminoalkylmethacrylamides and -acrylamides. Such compounds are described, for example, in U.S. Pat. No. 3,836,537.

Mention may also be made, for example, of the sodium acrylate/acrylamidopropyltrimethylammonium chloride copolymer sold under the name Polyquart KE 3033 by the company Cognis.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Nalco.

(2) polymers comprising units derived from:
a) at least one monomer chosen from acrylamides and methacrylamides substituted on the nitrogen with an alkyl radical,
b) at least one acidic comonomer comprising at least one reactive carboxylic group, and
c) at least one basic comonomer such as esters comprising substitutents chosen from primary, secondary, tertiary and quaternary amine substituents of acrylic and methacrylic acids and the product of quaternization of dimethylaminoethyl methacrylate with dimethyl or diethyl sulphate.

In one embodiment, the N-substituted acrylamides or methacrylamides according to the invention are, for example, groups in which the alkyl radicals comprise from 2 to 12 carbon atoms, such as N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen, for example, from acrylic acids, methacrylic acids, crotonic acids, itaconic acids, maleic acids and fumaric acids and alkyl monoesters, comprising from 1 to 4 carbon atoms, of maleic acids or fumaric acids or anhydrides.

The basic comonomers are chosen, for example, from aminoethyl, butylaminoethyl, N,N'-dimethylaminoethyl and N-tert-butylaminoethyl methacrylates.

The copolymers having the CTFA (4th edition, 1991) name octylacrylamide/acrylates/butylaminoethyl methacrylate copolymer such as the products sold under the name Amphomer or Lovocryl 47 by the company National Starch can, for example, also be used.

(3) crosslinked and partially or totally alkylated polyamino amides derived from polyamino amides of general formula:

$$\text{—[CO—R}_4\text{—CO-Z]—} \quad (IV)$$

wherein $R_4$ is chosen from a divalent radical derived from a saturated dicarboxylic acid, mono- and dicarboxylic aliphatic acids comprising an ethylenic double bond, an ester of a lower alkanol, comprising from 1 to 6 carbon atoms, of these acids and a radical derived from the addition of any one of the acids to amines chosen from bis(primary) and bis(secondary) amines, and Z is chosen from bis(primary), mono- and bis(secondary) polyalkylene-polyamine radicals and, for example, Z represents:

a) in proportions of from 60 to 100 mol %, the radical of formula (V)

$$\text{—NH—[(CH}_2)_x\text{—NH]}_p\text{—} \quad (V)$$

wherein x=2 and p=2 or 3, or x=3 and p=2, this radical being derived from a compound chosen from diethylenetriamine, triethylenetetraamine and dipropylenetriamine;

b) in proportions of from 0 to 40 mol %, the radical (V) above in which x=2 and p=1 and which is derived from a compound chosen from ethylenediamine and piperazine:

c) in proportions of from 0 to 20 mol %, the —NH—(CH$_2$)$_6$—NH— radical, which is derived from hexamethylenediamine, these polyaminoamines can be crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

In one embodiment, the saturated carboxylic acids are, for example, chosen from acids comprising from 6 to 10 carbon atoms, such as adipic acid, 2,2,4-trimethyladipic acid and 2,4,4-trimethyladipic acid, terephthalic acid, acids comprising an ethylenic double bond, such as acrylic acid, methacrylic acid and itaconic acid.

The alkane sultones used in the alkylation are chosen, for example, from propane sultone and butane sultone, and the salts of the alkylating agents can be chosen, for example, from sodium and potassium salts.

(4) polymers comprising zwitterionic units of formula (VI):

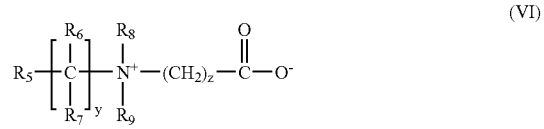

wherein $R_5$ is chosen from polymerizable unsaturated groups such as acrylate, methacrylate, acrylamide and methacrylamide groups, y and z, which may be identical or different, are chosen from integers from 1 to 3, $R_6$ and $R_7$, which may be identical or different, are chosen from a hydrogen atom, and methyl, ethyl and propyl groups, $R_8$ and $R_9$, which may be identical or different, are chosen from a hydrogen atom and alkyl radicals such that the sum of the carbon atoms in $R_8$ and $R_9$ does not exceed 10.

The polymers comprising such units can also comprise units derived from non-zwitterionic monomers such as monomers chosen from dimethyl and diethylaminoethyl acrylates and methacrylates, alkyl acrylates, methacrylates, acrylamides, methacrylamides and vinyl acetate.

By way of example, mention may be made of the copolymer of methyl methacrylate/dimethyl carboxymethylammonio methyl ethylmethacrylate such as the product sold under the name Diaformer Z301 by the company Sandoz.

(5) polymers derived from chitosan comprising monomer units corresponding to formulae (VII), (VIII) and (IX) below:

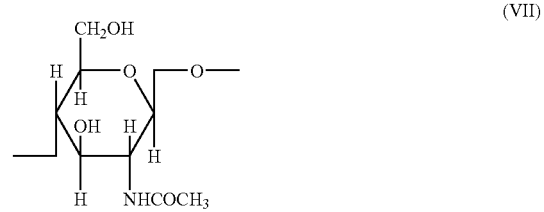

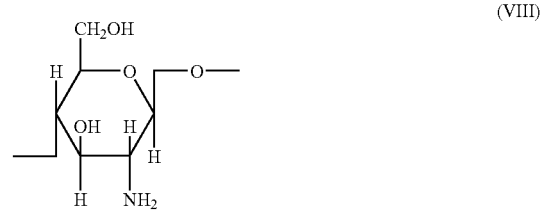

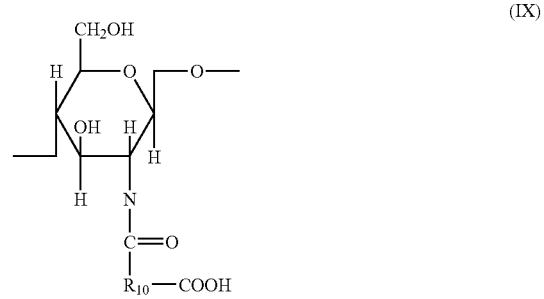

the unit (VII) being present in proportions ranging from 0 to 30%, the unit (VIII) in proportions ranging from 5 to 50% and the unit (IX) in proportions ranging from 30 to 90%, and wherein in the unit (IX), $R_{10}$ is a radical of formula:

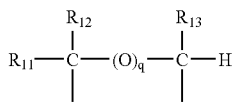

wherein q is equal to 0 or 1;

if q=0, $R_{11}$, $R_{12}$ and $R_{13}$, which may be identical or different, are chosen from a hydrogen atom, methyl, hydroxyl, acetoxy and amino residues, monoalkylamine residues and dialkylamine residues which are optionally interrupted by at least one nitrogen atom and/or optionally substituted with at least one group chosen from amine, hydroxyl, carboxyl, alkylthio and sulphonic groups, and alkylthio residues in which the alkyl group bears an amino residue, at least one of the radicals $R_{11}$, $R_{12}$ and $R_{13}$ being, in this case, a hydrogen atom;

or, if q=1, $R_{11}$, $R_{12}$ and $R_{13}$, which may be identical or different, are each chosen from a hydrogen atom, and salts formed by these compounds with bases or acids.

(6) Polymers derived from the N-carboxyalkylation of chitosan, such as N-carboxymethylchitosan and N-carboxybutylchitosan sold under the name "Evalsan" by the company Jan Dekker.

(7) Polymers corresponding to the general formula (X) such as those described, for example, in French Patent No. 1 400 366:

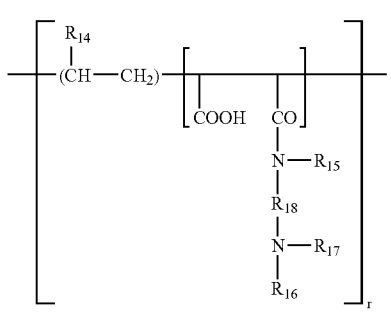

(X)

in which $R_{14}$ is chosen from a hydrogen atom, $CH_3O$, $CH_3CH_2O$ and phenyl radicals, $R_{15}$ is chosen from a hydrogen atom and lower alkyl radicals such as methyl and ethyl, $R_{16}$ is chosen from a hydrogen atom and lower alkyl radicals such as methyl and ethyl, $R_{17}$ is chosen from lower alkyl radicals such as methyl and ethyl radicals corresponding to the formula: $-R_{18}-N(R_{16})_2$, wherein $R_{18}$ is chosen from $-CH_2-CH_2-$, $-CH_2-CH_2-CH_2-$ and $-CH_2-CH(CH_3)-$ groups, and $R_{16}$ is chosen from a hydrogen atom and lower alkyl radicals such as methyl and ethyl, and the higher homologues of these radicals comprising up to 6 carbon atoms, r is chosen such that the number-average molecular weight of said polymer ranges from 500 to 6 000 000, such as from 1,000 to 1,000,000.

(8) Amphoteric polymers of the type -D-X-D-X chosen from:

a) polymers obtained by the action of chloroacetic acid or sodium chloroacetate on compounds comprising at least one unit of formula:

-D-X-D-X-D- (XI)

wherein D is a radical

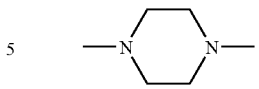

and X is chosen from the symbols E and E', wherein E and E', which may be identical or different, are chosen from divalent alkylene radicals comprising at least one chain chosen from straight and branched chains comprising up to 7 carbon atoms in the main chain, wherein said divalent alkylene radicals are unsubstituted or substituted with at least one hydroxyl group. E or E' can additionally comprise at least one atom chosen from oxygen, nitrogen and sulphur atoms, and 1 to 3 rings chosen from aromatic and heterocyclic rings. The oxygen, nitrogen and sulphur atoms can be present in the form of at least one group chosen from ether, thioether, sulphoxide, sulphone, sulphonium, alkylamine, and alkenylamine, hydroxyl, benzylamine, amine oxide, quaternary ammonium, amide, imide, alcohol, ester and urethane groups.

b) Polymers of formula:

-D-X-D-X- (XII)

wherein D is a radical

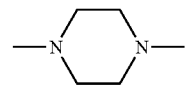

and X is chosen from the symbols E and E' and wherein at least one X is chosen from E'; E having the meaning given above and E' being a divalent radical chosen from divalent alkylene radicals comprising at least one chain chosen from straight and branched chains comprising up to 7 carbon atoms in the main chain, wherein said divalent alkylene radicals are optionally substituted with at least one hydroxyl radical and comprise at least one nitrogen atom substituted with an alkyl chain, which is optionally interrupted by an oxygen atom, and further comprising at least one functional group chosen from carboxyl functional groups and hydroxyl functional groups which are betainized by reaction with a reactant chosen from chloroacetic acid and sodium chloroacetate.

(9) $(C_1-C_5)$alkyl vinyl ether/maleic anhydride copolymers, the maleic anhydride being partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

In one embodiment, the amphoteric polymers are chosen from polymers of family (1).

In one embodiment, the nonionic polymers are chosen from the following polymers:

vinylpyrrolidone homopolymers;

copolymers of vinylpyrrolidone and vinyl acetate;

polyalkyloxazolines such as the polyethyloxazolines sold by the company Dow Chemical under the names Peox 50,000, Peox 200,000 and Peox 500 000;

vinyl acetate homopolymers, such as the product sold under the name Appretan EM by the company Hoechst, and the product sold under the name Rhodopas A 012 by the company Rhodia Chimie;

copolymers of vinyl acetate and acrylic ester, such as the product sold under the name Rhodopas AD 310 by Rhodia Chimie;

copolymers of vinyl acetate and ethylene, such as the product sold under the name Appretan TV by the company Hoechst;

copolymers of vinyl acetate and maleic ester, for example of dibutyl maleate, such as the product sold under the name Appretan MB Extra by the company Hoechst;

copolymers of polyethylene and maleic anhydride;

alkyl acrylate homopolymers and alkyl methacrylate homopolymers, such as the product sold under the name Micropearl RQ 750 by the company Matsumoto and the product sold under the name Luhydran A 848 S by the company BASF;

acrylic ester copolymers such as copolymers of alkyl acrylates and alkyl methacrylates, for example, the products sold by the company Rohm & Haas under the names Primal AC-261 K and Eudragit NE 30 D, by the company BASF under the names Acronal 601, Luhydran LR 8833 and 8845, and by the company Hoechst under the names Appretan N 9213 or N 9212;

copolymers of acrylonitrile and a nonionic monomer chosen, for example, from butadiene and alkyl (meth)acrylates; mention may be made of the products sold under the names Nipol LX 531 B by the company Nippon Zeon and those sold under the name CJ 0601 B by the company Rohm & Haas;

polyurethanes, such as the products sold under the names Acrysol RM 1020 and Acrysol RM 2020 by the company Rohm & Haas, and the products Uraflex XP 401 UZ and Uraflex XP 402 UZ by the company DSM Resins;

copolymers of alkyl acrylate and urethane, such as the product 8538-33 by the company National Starch;

polyamides, such as the product Estapor LO 11 sold by the company Rhodia Chimie; and unmodified and chemically modified nonionic guar gums.

The unmodified nonionic guar gums are, for example, the products sold under the name Vidogum GH 175 by the company Unipectine and under the name Jaguar C by the company Meyhall.

The modified nonionic guar gums are, for example, modified with at least one group chosen from $C_1$-$C_6$ hydroxyalkyl groups. Mention may be made, for example, of hydroxymethyl, hydroxyethyl, hydroxypropyl and hydroxybutyl groups.

These guar gums are well known in the state of the art and can be prepared, for example, by reacting corresponding alkene oxides, such as propylene oxides, with guar gum so as to obtain a guar gum modified with hydroxypropyl groups.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Meyhall and under the name Galactasol 4H4FD2 by the company Aqualon.

The alkyl radicals of the nonionic polymers comprise from 1 to 6 carbon atoms, except where otherwise mentioned.

Functionalized and non-functionalized polyurethanes may also be used as the polymers.

The polyurethanes are described in the documents of EP 0 751 162, EP 0 637 600, FR 2 743 297 and EP 0 648 485, and also the documents of EP 0 656 021 and WO 94/03510 from the company BASF and the document of EP 0 619 111 from the company National Starch.

The conditioners of cationic polymer type may be chosen from any of those already known by those skilled in the art as improving at least one of the cosmetic properties of hair treated with detergent compositions, for example, those described in European patent application EP-A-0 337 354 and in French patent applications FR-A-2 270 846, 2 383 660, 2 598 611, 2 470 596 and 2 519 863.

Even more generally, the expression "cationic polymer" denotes any polymer containing cationic groups and/or groups that may be ionized into cationic groups.

The cationic polymers are, for example, chosen from those comprising units comprising at least one amine group chosen from primary, secondary, tertiary and quaternary amine groups that may either form part of the main polymer chain, or be borne by a side substituent that is directly attached to the said main polymer chain.

The cationic polymers used generally have a number-average molar mass ranging, for example, from 500 to $5 \times 10^6$ approximately and such as from $10^3$ to $3 \times 10^6$ approximately.

Among the cationic polymers, mention may be made, for example, of polymers of the polyamine, polyamino amide and polyquaternary ammonium type. These are known polymers.

The polymers of the polyamine, polyamino amide and polyquaternary ammonium type that may be used, for example, are those described in French patents 2 505 348 and 2 542 997. Among these polymers, mention may be made of:

(1) homopolymers and copolymers derived from acrylic or methacrylic esters or amides and comprising at least one of the units of the following formulae:

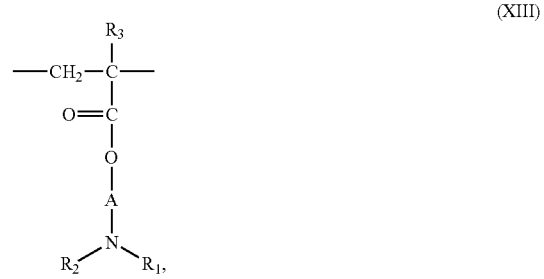

(XIII)

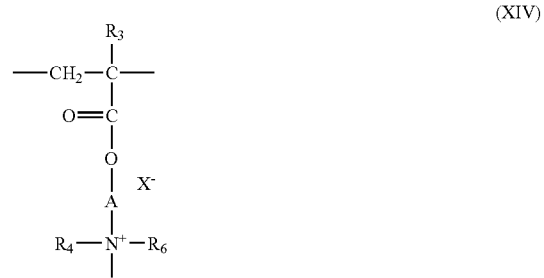

(XIV)

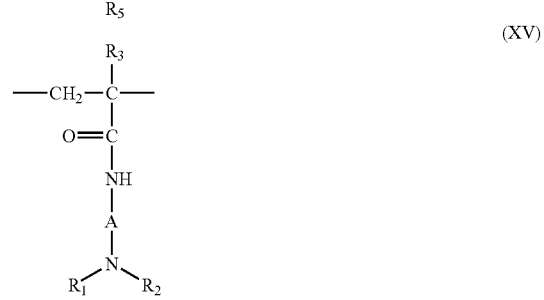

(XV)

-continued

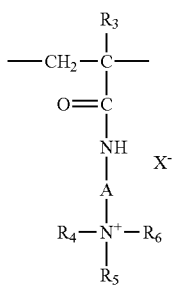

(XVI)

in which:

R$_1$ and R$_2$, which may be identical or different, are chosen from hydrogen and alkyl groups comprising from 1 to 6 carbon atoms, and such as methyl and ethyl groups;

R$_3$, which may be identical or different, are chosen from a hydrogen atom and a CH$_3$ radical;

A, which may be identical or different, is chosen from linear and branched alkyl groups of 1 to 6 carbon atoms, such as 2 or 3 carbon atoms, and hydroxyalkyl groups of 1 to 4 carbon atoms;

R$_4$, R$_5$ and R$_6$, which may be identical or different, are chosen from alkyl groups comprising from 1 to 18 carbon atoms and benzyl radicals and such as alkyl groups comprising from 1 to 6 carbon atoms;

X$^-$ is an anion derived from a mineral or organic acid, such as a methosulphate anion or an anion chosen from halides such as chloride and bromide.

Copolymers of family (1) can also comprise at least one unit derived from comonomers which may be chosen from the family of acrylamides, methacrylamides, diacetone acrylamides, acrylamides and methacrylamides substituted on the nitrogen with at least one group chosen from lower (C$_1$-C$_4$) alkyls, acrylic and methacrylic acids and esters thereof, vinyllactams such as vinylpyrrolidone and vinylcaprolactam, and vinyl esters.

Thus, among these copolymers of family (1), mention may be made of:

the copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba, the copolymer of acrylamide and of methacryloyloxyethyltrimethylammonium methosulphate sold under the name Reten by the company Hercules, quaternized or non-quaternized vinylpyrrolidone/dialkylaminoalkyl acrylate or methacrylate copolymers, such as the products sold under the name "Gafquat" by the company ISP, such as "Gafquat® 734" or "Gafquat® 755", or the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix® VC 713 by the company ISP, vinylpyrrolidone/methacrylamidopropyldimethylamine copolymers sold, for example, under the name Styleze® CC 10 by ISP, and quaternized vinylpyrrolidone/dimethylaminopropylmethacrylamide copolymers such as the product sold under the name "Gafquat® HS 100" by the company ISP.

(2) cationic polysaccharides, such as cationic celluloses and cationic galactomannan gums. Among the cationic polysaccharides that may be mentioned, for example, are cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups, which are described in French Patent No. 1 492 597, and, for example, the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

The cationic cellulose copolymers or cellulose derivatives grafted with a water-soluble quaternary ammonium monomer are described, for example, in U.S. Pat. No. 4,131,576, such as hydroxyalkylcelluloses, for instance hydroxymethyl-, hydroxyethyl- or hydroxypropylcelluloses grafted, for example, with a salt chosen from methacryloylethyltrimethylammonium, methacrylamidopropyltrimethylammonium and dimethyldiallylammonium salts.

The commercial products corresponding to this definition are, for example, the products sold under the name "Celquat® L 200" and "Celquat® H 100" by the company National Starch.

The cationic galactomannan gums are described, for example, in U.S. Pat. Nos. 3,589,578 and 4,031,307, such as guar gums comprising trialkylammonium cationic groups. For example, guar gums modified with a salt (e.g. chloride) of 2,3-epoxypropyltrimethylammonium may be used.

Such polymers are sold, for example, under the trade names Jaguar® C13S, Jaguar® C15, Jaguar® C17 and Jaguar® C162 by the company Meyhall.

(3) polymers comprising piperazinyl units and divalent alkylene or hydroxyalkylene radicals comprising straight or branched chains, optionally interrupted with at least one atom chosen from oxygen, sulphur and nitrogen atoms or with at least one ring chosen from aromatic and heterocyclic rings, and at least one of the oxidation and quaternization products of these polymers. Such polymers are described, for example, in French Patent Nos. 2 162 025 and 2 280 361;

(4) water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative. The crosslinking agent can be used in proportions ranging from 0.025 to 0.35 mol per amine group of the polyamino amide. These polyamino amides can be alkylated or, if they comprise at least one tertiary amine function, they can be quaternized. Such polymers are described, for example, in French Patent Nos. 2 252 840 and 2 368 508;

(5) polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and such as methyl, ethyl and propyl. Such polymers are described, for example, in French Patent No. 1 583 363.

Among these derivatives, mention may be made, for example, of the adipic acid/dimethylaminohydroxypropyl/diethylenetriamine polymers sold under the name "Cartaretine® F, F4 or F8" by the company Sandoz.

(6) polymers obtained by reaction of a polyalkylene polyamine comprising two primary amine groups and at least one secondary amine group with a dicarboxylic acid chosen from diglycolic acids and saturated aliphatic dicarboxylic acids comprising from 3 to 8 carbon atoms. The molar ratio between the polyalkylene polyamine and the dicarboxylic acid may range, for example, from 0.8:1 to 1.4:1; the polyamino amide resulting therefrom may be reacted with epichlorohydrin in a molar ratio of epichlorohydrin relative to the secondary amine group of the polyamino amide ranging from 0.5:1 to 1.8:1.Such polymers are described, for example, in U.S. Pat. Nos. 3,227,615 and 2,961,347.

Other non-limiting examples of such derivatives include the adipic acid/epoxypropyl/diethylenetriamine copolymer sold, for example, under the name "Hercosett® 57" by the company Hercules Inc. or under the name "PD 170" or "Delsette® 101" by the company Hercules.

(7) cyclopolymers of alkyldiallylamine or of dialkyldiallylammonium, such as the homopolymers or copolymers comprising, as main constituent of the chain, at least one unit corresponding to formula (XVII) or (XVIII):

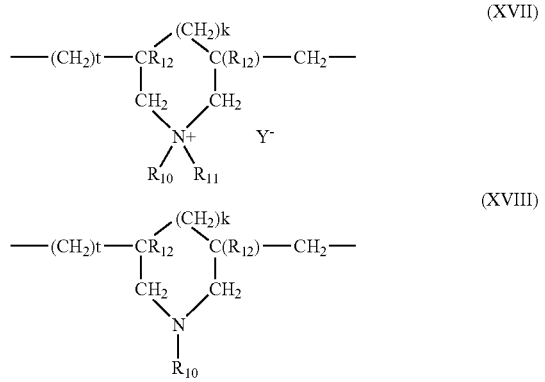

in which k and t are equal to 0 or 1, the sum k+t being equal to 1;

$R_{12}$ is chosen from a hydrogen atom and a methyl radical;

$R_{10}$ and $R_{11}$, which may be identical or different, are chosen from alkyl groups comprising from 1 to 8 carbon atoms, hydroxyalkyl groups in which the alkyl group, for example, comprises from 1 to 5 carbon atoms, and lower ($C_1$-$C_4$) amidoalkyl groups, or $R_{10}$ and $R_{11}$ are chosen from, together with the nitrogen atom to which they are attached, heterocyclic groups such as piperidyl or morpholinyl; $Y^-$ is an anion such as bromide, chloride, acetate, borate, citrate, tartrate, bisulphate, bisulphite, sulphate and phosphate. These polymers are described, for example, in French Patent No. 2 080 759 and in its Certificate of Addition 2 190 406.

In one embodiment, $R_{10}$ and $R_{11}$, which may be identical or different, are, for example, chosen from alkyl groups comprising from 1 to 4 carbon atoms.

Among the polymers defined above, mention may be made, for example, of the dimethyldiallylammonium chloride homopolymer sold under the name "Merquat® 100" by the company Nalco (and its homologues of low weight-average molecular mass) and copolymers of diallyldimethylammonium chloride and of acrylamide, sold under the name "Merquat® 550".

(8) quaternary diammonium polymers comprising repeating units corresponding to the formula (XIX):

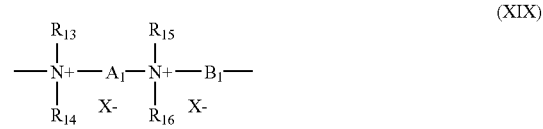

in which:

$R_{13}$, $R_{14}$, $R_{15}$ and $R_{16}$, which may be identical or different, are chosen from aliphatic, alicyclic and arylaliphatic radicals comprising from 1 to 20 carbon atoms and from lower hydroxyalkylaliphatic radicals, or $R_{13}$, $R_{14}$, $R_{15}$ and $R_{16}$, together or separately, constitute, with the nitrogen atoms to which they are attached, heterocycles optionally comprising a second hetero atom other than nitrogen, or $R_{13}$, $R_{14}$, $R_{15}$ and $R_{16}$ are chosen from linear and branched $C_1$-$C_6$ alkyl radicals substituted with at least one group chosen from nitrile, ester, acyl and amide groups and groups of —CO—O—$R_{17}$-D and —CO—NH—$R_{17}$-D wherein $R_{17}$ is chosen from alkylene groups and D is chosen from quaternary ammonium groups;

$A_1$ and $B_1$, which may be identical or different, are chosen from linear and branched, saturated and unsaturated polymethylene groups comprising from 2 to 20 carbon atoms. The polymethylene groups may comprise, linked to or intercalated in the main chain, at least one entity chosen from aromatic rings, oxygen and sulphur atoms and sulphoxide, sulphone, disulphide, amino, alkylamino, hydroxyl, quaternary ammonium, ureido, amide and ester groups, and $X^-$ is an anion chosen from anions derived from mineral acids and organic acids;

$A_1$, $R_{13}$ and $R_{15}$ may optionally form, with the two nitrogen atoms to which they are attached, a piperazine ring; in addition, if $A_1$ is a radical chosen from linear and branched, saturated and unsaturated alkylene and hydroxyalkylene radicals, $B_1$ can also represent a group $(CH_2)_n$—CO-D-OC—$(CH_2)_2$—, in which n ranges from 1 to 100, such as from 1 to 50, and D is chosen from:

a) a glycol residue of formula: —O-Z-O—, wherein Z is chosen from linear and branched hydrocarbon-based radicals and a group corresponding to one of the following formulae:

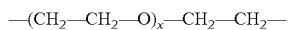

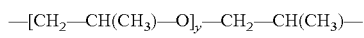

wherein x and y, which may be identical or different, are each an integer ranging from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, wherein Y is chosen from linear and branched hydrocarbon-based radicals, and the divalent radical —$CH_2$—$CH_2$—S—S—$CH_2$—$CH_2$—; and d) a ureylene group of formula: —NH—CO—NH—.

For example, X⁻ is an anion such as chloride or bromide.

These polymers may have a number-average molecular mass ranging from 1000 to 100,000.

These polymers are described, for example, in French Patent Nos. 2,320 330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, polymers can comprise repeating units corresponding to the formula (XX):

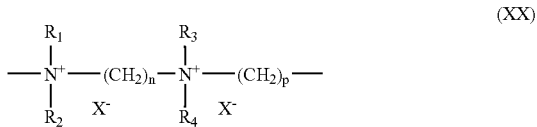

in which $R_1$, $R_2$, $R_3$ and $R_4$, which may be identical or different, are chosen from alkyl and hydroxyalkyl radicals comprising from 1 to 4 carbon atoms, n and p, which may be identical or different, are integers ranging from 2 to 20, and X⁻ is an anion chosen from anions derived from mineral acids and organic acids.

One compound of formula (XX), for example, is the one for which $R_1$, $R_2$, $R_3$ and $R_4$ are each a methyl radical and n=3, p=6 and X=Cl, which is known as Hexadimethrine chloride according to the INCI (CTFA) nomenclature.

(9) polyquaternary ammonium polymers comprising repeating units of formula (XXI):

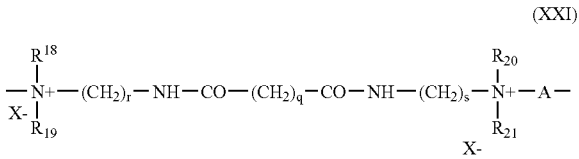

in which:

$R_{18}$, $R_{19}$, $R_{20}$ and $R_{21}$, which may be identical or different, are chosen from a hydrogen atom and methyl, ethyl, propyl, β-hydroxyethyl, β-hydroxypropyl and —CH₂CH₂(OCH₂CH₂)ₚOH radicals, wherein p is equal to 0 or to an integer ranging from 1 to 6, with the proviso that $R_{18}$, $R_{19}$, $R_{20}$ and $R_{21}$ do not simultaneously represent a hydrogen atom, r and s, which may be identical or different, are each an integer ranging from 1 to 6, q is equal to 0 or to an integer ranging from 1 to 34, X⁻ is an anion such as a halide, A is chosen from divalent radicals, such as —CH₂—CH₂—O—CH₂—CH₂—.

Such polymers are described, for example, in patent application EP-A-122 324.

Among these polymers, mention may be made, for example, of "Mirapol® A 15", "Mirapol® AD1", "Mirapol® AZ1" and "Mirapol® 175" sold by the company Miranol.

(10) quaternary polymers of vinylpyrrolidone and of vinylimidazole, such as the products sold under the names Luviquat® FC 905, FC 550 and FC 370 by the company BASF.

(11) polyamines such as the product Polyquart® H sold by Cognis under the reference name "Polyethylene Glycol (15) Tallow Polyamine" in the CTFA dictionary.

(12) crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. In one embodiment, a crosslinked acrylamide/methacryloyloxyethyltrimethylammonium chloride copolymer (20/80 by weight) in the form of a dispersion comprising 50% by weight of the said copolymer in mineral oil may be used. This dispersion is sold under the name "Salcare® SC 92" by the company Ciba. In another embodiment, a crosslinked homopolymer of methacryloyloxyethyltrimethylammonium chloride comprising about 50% by weight of the homo-polymer in mineral oil or in a liquid ester may be used. These dispersions are sold under the names "Salcare® SC 95" and "Salcare® SC 96" by the company Ciba.

Other cationic polymers which can be used are chosen from cationic proteins and cationic protein hydrolysates, polyalkyleneimines, such as polyethyleneimines, polymers comprising units chosen from vinylpyridine and vinylpyridinium units, condensates of polyamines and of epichlorohydrin, quaternary polyureylenes and chitin derivatives.

Among all the cationic polymers that may be used, non-limiting examples include quaternary cellulose ether derivatives such as the products sold under the name "JR 400" by the company Amerchol, cationic cyclopolymers, such as the dimethyldiallylammonium chloride homopolymers and copolymers sold under the names "Merquat® 100", "Merquat® 550" and "Merquat® S" by the company Nalco, quaternary polymers of vinylpyrrolidone and of vinylimidazole, and mixtures thereof.

The cationic proteins or protein hydrolysates can be, for example, chemically modified polypeptides bearing quaternary ammonium groups at the end of the chain or grafted thereto. Their molecular mass may range, for example, from 1500 to 10 000 and further, for example, from 2000 to 5000. Among these compounds, mention may be made of:

collagen hydrolysates bearing triethylammonium groups, such as the products sold under the name "Quat-Pro E" by the company Maybrook and referred to in the CTFA dictionary as "Triethonium Hydrolyzed Collagen Ethosulphate";

collagen hydrolysates bearing trimethylammonium and trimethylstearylammonium chloride groups, sold under the name "Quat-Pro S" by the company Maybrook and referred to in the CTFA dictionary as "Steartrimonium Hydrolyzed Collagen";

animal protein hydrolysates bearing trimethylbenzylammonium groups such as the products sold under the name "Crotein® BTA" by the company Croda and referred to in the CTFA dictionary as "Benzyltrimonium hydrolyzed animal protein"; and protein hydrolysates bearing, on the polypeptide chain, quaternary ammonium groups comprising at least one alkyl radical comprising from 1 to 18 carbon atoms.

Among these protein hydrolysates, mention may be made of, inter alia:

"Croquat® L" in which the quaternary ammonium groups comprise a $C_{12}$ alkyl group;

"Croquat® M" in which the quaternary ammonium groups comprise $C_{10}$-$C_{18}$ alkyl groups;

"Croquat® S" in which the quaternary ammonium groups comprise a $C_{18}$ alkyl group;

"Crotein® Q" in which the quaternary ammonium groups comprise at least one alkyl group comprising from 1 to 18 carbon atoms.

These various products are sold by the company Croda.

Other quaternized proteins or hydrolysates are, for example, those corresponding to the formula (XXII):

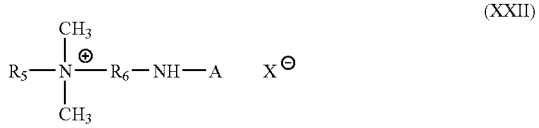
(XXII)

in which:

X⁻ is an anion chosen from anions derived from organic and inorganic acids,

A is a protein residue derived from hydrolysates of a protein, for example, of collagen, $R_5$ is chosen from lipophilic groups comprising up to 30 carbon atoms and $R_6$ is chosen from alkylene groups comprising from 1 to 6 carbon atoms.

Mention may be made, for example, of the products sold by the company Inolex under the name "Lexein® QX 3000", referred to in the CTFA dictionary as "Cocotrimonium Collagen Hydrolysate".

Mention may further be made, for example, of quaternized plant proteins such as wheat, corn and soybean proteins: as quaternized wheat proteins, mention may be made of those sold by the company Croda under the names "Hydrotriticum WQ or QM", referred to in the CTFA dictionary as "Cocodimonium Hydrolysed Wheat Protein", "Hydrotriticum QL", referred to in the CTFA dictionary as "Lauridimonium Hydrolysed Wheat Protein" and "Hydrotriticum QS", referred to in the CTFA dictionary as "Steardimonium Hydrolysed Wheat Protein".

The cationic surfactants are, for example, chosen from quaternary ammonium salts, quaternary ammonium salts of imidazoline, diquaternary ammonium salts, and quaternary ammonium salts comprising at least one ester function.

The cationic surfactants may be chosen from:

A) the quaternary ammonium salts of general formula (XXIII) below:

(XXIII)

wherein X⁻ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and i) the radicals $R_1$ to $R_3$, which may be identical or different, are chosen from a linear and branched aliphatic radical comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy and alkylamide radicals, $R_4$ is chosen from linear and branched alkyl radicals comprising from 16 to 30 carbon atoms.

The cationic surfactant is, for example, a behenyltrimethylammonium salt (for example chloride).

ii) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy, alkylamide and hydroxyalkyl radicals comprising from about 1 to 4 carbon atoms;

$R_3$ and $R_4$, which may be identical or different, are chosen from linear and branched alkyl radicals comprising from 12 to 30 carbon atoms, the said alkyl radicals may comprise at least one function chosen from ester and amide functions.

$R_3$ and $R_4$ are chosen, for example, from ($C_{12}$-$C_{22}$)alkylamido($C_2$-$C_6$)alkyl and ($C_{12}$-$C_{22}$)alkylacetate radicals.

The cationic surfactant is, for example, a stearamidopropyldimethyl(myristyl acetate)ammonium salt (for example chloride);

B)—the quaternary ammonium salts of imidazolinium, such as that of formula (XXIV) below:

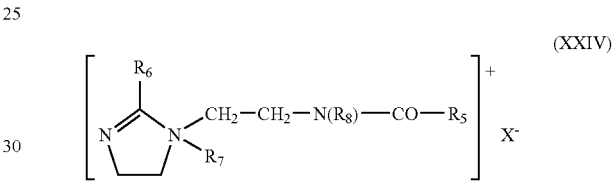
(XXIV)

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_8$ is chosen from a hydrogen atom and $C_1$-$C_4$ alkyl radicals, and X⁻ is an anion chosen from halides, phosphates, acetates, lactates, alkyl sulphates, alkyl sulphonates and alkylaryl sulphonates.

In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat®" W75, W90, W75PG and W75HPG by the company Witco, C)—the diquaternary ammonium salts of formula (XXV):

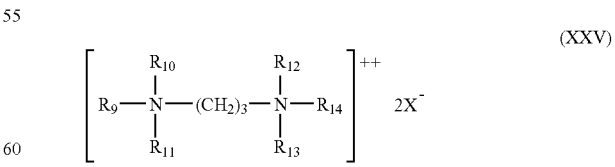
(XXV)

in which $R_9$ is chosen from aliphatic radicals comprising from 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates.

Such diquaternary ammonium salts, for example, include propanetallowdiammmonium dichloride; and D)—the quaternary ammonium salts comprising at least one ester function, of formula (XXVI) below:

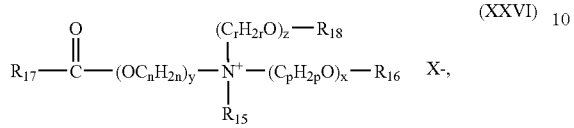

in which:

$R_{15}$ is chosen from $C_1$-$C_6$ alkyl radicals and $C_1$-$C_6$ hydroxyalkyl and dihydroxyalkyl radicals;

$R_{16}$ is chosen from:
a radical

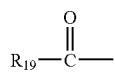

linear and branched, saturated and unsaturated $C_1$-$C_{22}$ hydrocarbon-based radicals $R_{20}$, and a hydrogen atom, $R_{18}$ is chosen from:
a radical

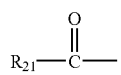

linear and branched, saturated and unsaturated $C_1$-$C_6$ hydrocarbon-based radicals $R_{22}$, and a hydrogen atom, $R_{17}$, $R_{19}$ and $R_{21}$, which may be identical or different, are chosen from linear and branched, saturated and unsaturated $C_7$-$C_{21}$ hydrocarbon-based radicals;

n, p and r, which may be identical or different, are chosen from integers ranging from 2 to 6;

y is chosen from integers ranging from 1 to 10;

x and z, which may be identical or different, are chosen from integers ranging from 0 to 10;

$X^-$ is an anion chosen from simple and complex, organic and inorganic anions;

with the proviso that the sum x+y+z is from 1 to 15, that when x is 0, then $R_{16}$ is $R_{20}$ and that when z is 0, then $R_{18}$ is $R_{22}$.

In one embodiment, the ammonium salts of formula (XXVI) can be used, in which:

$R_{15}$ is chosen from methyl and ethyl radicals, x and y are equal to 1;

z is equal to 0 or 1;

n, p and r are equal to 2;

$R_{16}$ is chosen from:
a radical

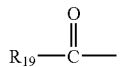

methyl, ethyl and $C_{14}$-$C_{22}$ hydrocarbon-based radicals, and a hydrogen atom;

$R_{17}$, $R_{19}$ and $R_{21}$, which may be identical or different, are chosen from linear and branched, saturated and unsaturated $C_7$-$C_{21}$ hydrocarbon-based radicals;

$R_{18}$ is chosen from:
a radical

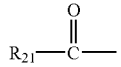

and
a hydrogen atom.

Such compounds are sold, for example, under the names Dehyquart® by the company Cognis, Stepanquat® by the company Stepan, Noxamium® by the company Ceca, and Rewoquat® WE 18 by the company Rewo-Witco.

Among the quaternary ammonium salts, examples are stearamidopropyldimethyl(myristyl acetate)ammonium chloride, sold under the name "Ceraphyl® 70" by the company Van Dyk, and Quaternium-27 or Quaternium-83 sold by the company Witco.

The cationic surfactants are classified in the category of soluble conditioners, but, depending on their chemical structures, some cationic surfactants may be water-insoluble.

The at least one conditioner may be in a concentration ranging from 0.001% to 20% by weight, for example, from 0.01% to 10% by weight and further, for example, from 0.1% to 3% by weight relative to the total weight of the composition.

In one embodiment, the compositions comprise at least one entity chosen from cationic polymers and silicones.

The compositions can also comprise at least one surfactant, which is generally present in an amount ranging, for example, from 0.1% to 60% by weight, such as from 3% to 40% and further such as from 5% to 30% relative to the total weight of the composition.

This at least one surfactant may be chosen from anionic, amphoteric, nonionic and cationic surfactants.

The at least one surfactant that is suitable is, for example, chosen from:

(i) Anionic Surfactants:

In the context of the present disclosure, their nature is not critical.

As examples of anionic surfactants, which can be used, alone or as mixtures, mention may be made, for example, of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates. The alkyl or acyl radical of all of these various compounds, for example, comprises from 8 to 24 carbon atoms, and the aryl radical, for example, is chosen from phenyl and benzyl groups. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof.

Among the anionic surfactants, for example, alkyl sulphate salts and alkyl ether sulphate salts and mixtures thereof can be used.

(ii) Nonionic Surfactants:

The nonionic surfactants are compounds that are well known (see, for example, in this respect "Handbook of Surfactants" by M. R. Porter, published by Blackie & Son (Glasgow and London), 1991, pp. 116-178) and in the present disclosure, the nature of the nonioinic surfactant is not critical. They can be chosen, for example, from polyethoxylated, polypropoxylated and polyglycerolated fatty acids, alkylphenols, a-diols and alcohols comprising a fatty chain comprising, for example, from 8 to 18 carbon atoms, it being possible for the number of ethylene oxide or propylene oxide groups to range, for example, from 2 to 50 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides, for example, comprising from 2 to 30 mol of ethylene oxide, polyglycerolated fatty amides comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides. It may be noted that the alkylpolyglycosides constitute nonionic surfactants that can be used.

(iii) Amphoteric Surfactants:

The amphoteric surfactants, whose nature is not critical, can be chosen, for example, from aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate and phosphonate); mention may also be made of ($C_8$-$C_{20}$)alkylbetaines, sulphobetaines, ($C_8$-$C_{20}$) alkylamido($C_1$-$C_6$)alkylbetaines or ($C_8$-$C_{20}$)alkylamido($C_1$-$C_6$)alkylsulphobetaines.

Among the amine derivatives, mention may be made of the products sold under the name Miranol, as described, for example, in U.S. Pat. Nos. 2,528,378 and 2,781,354 and having the structures of:

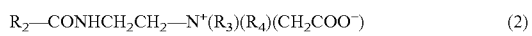

$$R_2-CONHCH_2CH_2-N^+(R_3)(R_4)(CH_2COO^-) \quad (2)$$

in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of

$$R_5-CONHCH_2CH_2-N(B)(C) \quad (3)$$

wherein B represents —$CH_2CH_2OX'$, C represents —$(CH_2)_z$—Y', with z=1 or 2, X' is chosen from the —$CH_2CH_2$—COOH group and a hydrogen atom, Y' is chosen from —COOH and —$CH_2$—CHOH—$SO_3H$ radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylam-phodipropionate, disodium caplyloamphodipropionate, lauroamphodipropionic acid, and cocoamphodipropionic acid.

By way of example, mention may be made of the cocoamphodiacetate sold under the trade name Miranol C2M concentrate by the company Rhodia Chimie.

(iv) Cationic Surfactants:

The cationic surfactants may be chosen from:

A) the quaternary ammonium salts of general formula (IX) below:

wherein $X^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and i) the radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy and alkylamide radicals, $R_4$ is chosen from linear and branched alkyl radicals comprising from 16 to 30 carbon atoms.

The cationic surfactant is, for example, a behenyltrimethylammonium salt (for example chloride).

ii) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atoms such as oxygen, nitrogen, sulphur and halogens. The aliphatic radicals are chosen, for example, from alkyl, alkoxy, alkylamide and hydroxyalkyl radicals comprising from 1 to 4 carbon atoms;

$R_3$ and $R_4$, which may be identical or different, are chosen from linear and branched alkyl radicals comprising from 12 to 30 carbon atoms, the said alkyl radicals may comprise at least one function chosen from ester and amide functions.

$R_3$ and $R_4$ are chosen, for example, from $(C_{12}-C_{22})$alkylamido$(C_2-C_6)$alkyl and $(C_{12}-C_{22})$alkylacetate radicals.

The cationic surfactant is, for example, a stearamidopropyldimethyl(myristyl acetate)ammonium salt (for example chloride);

B)—the quaternary ammonium salts of imidazolinium, such as that of formula (X) below:

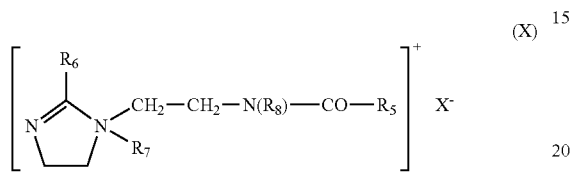

in which $R_5$ is chosen from alkenyl and alkyl radicals comprising from 8 to 30 carbon atoms, for example fatty acid derivatives of tallow, $R_6$ is chosen from a hydrogen atom, $C_1-C_4$ alkyl radicals and alkenyl and alkyl radicals comprising from 8 to 30 carbon atoms, $R_7$ is chosen from $C_1-C_4$ alkyl radicals, $R_8$ is chosen from a hydrogen atom and $C_1-C_4$ alkyl radicals, and $X^-$ is an anion chosen from halides, phosphates, acetates, lactates, alkyl sulphates, alkyl sulphonates and alkylaryl sulphonates.

In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat®" W75, W90, W75PG and W75HPG by the company Witco, C)—the diquaternary ammonium salts of formula (XI):

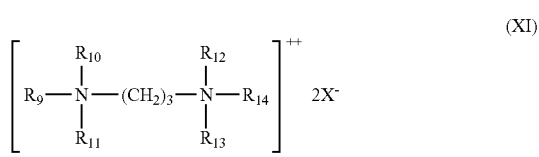

in which $R_9$ is chosen from aliphatic radicals comprising from 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates.

Such diquaternary ammonium salts, for example, include propanetallowdiammmonium dichloride; and D)—the quaternary ammonium salts comprising at least one ester function, of formula (XII) below:

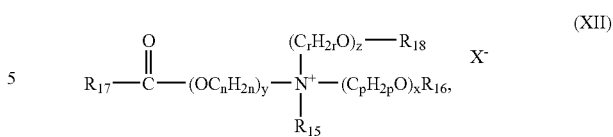

in which:
$R_{15}$ is chosen from $C_1-C_6$ alkyl radicals and $C_1-C_6$ hydroxyalkyl and dihydroxyalkyl radicals;
$R_{16}$ is chosen from:
a radical

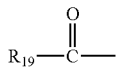

linear and branched, saturated and unsaturated $C_1-C_{22}$ hydrocarbon-based radicals $R_{20}$, and
a hydrogen atom,
$R_{18}$ is chosen from:
a radical

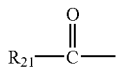

linear and branched, saturated and unsaturated $C_1-C_6$ hydrocarbon-based radicals $R_{22}$, and
a hydrogen atom,
$R_{17}$, $R_{19}$ and $R_{21}$, which may be identical or different, are chosen from linear and branched, saturated and unsaturated $C_7-C_{21}$ hydrocarbon-based radicals;
n, p and r, which may be identical or different, are chosen from integers ranging from 2 to 6;
y is chosen from integers ranging from 1 to 10;
x and z, which may be identical or different, are chosen from integers ranging from 0 to 10;
$X^-$ is an anion chosen from simple and complex, organic and inorganic anions;
with the proviso that the sum x+y+z is from 1 to 15, that when x is 0, then $R_{16}$ is $R_{20}$ and that when z is 0, then $R_{18}$ is $R_{22}$.

In one embodiment, the ammonium salts of formula (XII) can be used, in which:
$R_{15}$ is chosen from methyl and ethyl radicals,
x and y are equal to 1;
z is equal to 0 or 1;
n, p and r are equal to 2;
$R_{16}$ is chosen from:
a radical

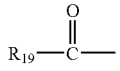

methyl, ethyl and $C_{14}-C_{22}$ hydrocarbon-based radicals, and
a hydrogen atom;
$R_{17}$, $R_{19}$ and $R_{21}$, which may be identical or different, are chosen from linear and branched, saturated and unsaturated $C_7-C_{21}$ hydrocarbon-based radicals;

$R_{18}$ is chosen from:
a radical

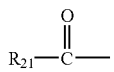

and
a hydrogen atom.

Such compounds are sold, for example, under the names Dehyquart® by the company Cognis, Stepanquat® by the company Stepan, Noxamium® by the company Ceca, and Rewoquat® WE 18 by the company Rewo-Witco.

Among the quaternary ammonium salts, examples are behenyltrimethylammonium chloride and also stearamidopropyldimethyl(myristyl acetate)ammonium chloride, sold under the name "Ceraphyl® 70" by the company Van Dyk, and Quaternium-27 or Quaternium-83 sold by the company Witco.

Among the anionic surfactants, sodium, triethanolamine and ammonium ($C_{12}$-$C_{14}$)alkyl sulphates, sodium, triethanolamine and ammonium ($C_{12}$-$C_{14}$)alkyl ether sulphates oxyethylenated with 2.2 mol of ethylene oxide, sodium cocoyl isethionate and sodium α-($C_{14}$-$C_{16}$)olefin sulphonate, and mixtures thereof can be used, with:

either an amphoteric surfactant such as the amine derivatives known as disodium cocoamphodipropionate or sodium cocoamphopropionate sold especially by the company Rhodia Chimie under the trade name "Miranol® C2M CONC" as an aqueous solution comprising 38% active material, or under the name Miranol® C32;

or an amphoteric surfactant such as alkylbetaines, such as the cocobetaine sold under the name "Dehyton® AB 30" as an aqueous solution comprising 32% active material by the company Cognis, or ($C_8$-$C_{20}$)alkylamido($C_1$-$C_6$) alkylbetaines, for example, Tegobetaine® F50 sold by the company Goldschmidt.

The composition may also comprise at least one additive chosen from thickeners, antidandruff and anti-seborrhoeic agents, fragrances, nacreous agents, hydroxy acids, electrolytes, preserving agents, silicone and non-silicone sunscreens, vitamins, provitamins such as panthenol, anionic and nonionic polymers, proteins, protein hydrolysates, 18-methyleicosanoic acid, and also mixtures of these various compounds and any other additive usually used in cosmetics that does not affect the properties of the compositions.

These additives are present in the composition in proportions that may range from 0 to 20% by weight relative to the total weight of the composition. The precise amount of each additive is readily determined by a person skilled in the art, depending on its nature and its function.

The compositions i may be used, for example, for washing or treating keratin materials such as the hair, the skin, the eyelashes, the eyebrows, the nails, the lips or the scalp.

In one embodiment, the compositions are detergent compositions such as shampoos, shower gels and bubble baths. In this embodiment, the compositions comprise at least one washing base, which is generally aqueous.

The at least one washing base comprises at least one surfactant. The at least one surfactant may be chosen, without discrimination, alone or as mixtures, from the anionic, amphoteric and nonionic surfactants as defined above.

The quantity and quality of the washing base are those that are sufficient to be able to give the final composition satisfactory foaming power and/or detergent power.

Thus, the washing base can be in an amount ranging, for example, from 4% to 50% by weight, such as from 6% to 35% by weight and further such as from 8% to 25% by weight, relative to the total weight of the composition.

Another new embodiment is a process for treating a keratin material such as the skin or the hair, characterized in that the process comprises applying to the keratin material a cosmetic composition as defined above, and then optionally rinsing it out with water.

Thus, this process can allow the maintenance of the hairstyle and the treatment, care and washing or the removal of makeup from the skin, the hair or any other keratin material.

The compositions may also be in the form of rinse-out or leave-in conditioners, permanent-waving, hair-straightening, dyeing or bleaching compositions, or in the form of rinse-out compositions to be applied before or after dyeing, bleaching, permanent-waving or straightening the hair or between the two steps of a permanent-waving or hair-straightening operation.

When the composition is in the form of a conditioner, such as a rinse-out conditioner, it, for example, comprises at least one cationic surfactant, and its concentration generally ranges, for example, from 0.1% to 10% by weight, and such as from 0.5% to 5% by weight, relative to the total weight of the composition.

The compositions may also be in the form of washing compositions for the skin, such as in the form of bath or shower solutions or gels or makeup-removing products.

The compositions may also be in the form of aqueous or aqueous-alcoholic lotions for skincare and/or haircare.

The cosmetic compositions may be in the form of a gel, a milk, a cream, an emulsion, a thickened lotion or a mousse and may be used for the skin, the nails, the eyelashes, the lips and, for example, the hair.

The compositions may be packaged in various forms, such as in vaporizers, pump-dispenser bottles or in aerosol containers to allow the composition to be applied in vaporized form or in the form of a mousse. Such packaging forms are indicated, for example, when it is desired to obtain a spray, a lacquer or a mousse for treating a keratin material, such as the hair.

Throughout the text hereinabove and hereinbelow, the percentages expressed are on a weight basis.

New embodiments will now be illustrated more fully with the aid of the examples that follow, which cannot be considered as limiting it to the specific embodiments described.

In the examples, AM means active material.

EXAMPLE 1

A shampoo having the composition below was prepared:

| | in g AM |
|---|---|
| Sodium lauryl ether sulphate (70/30 C12/C14) with 2.2 mol of ethylene oxide, containing 70% AM | 7 |
| Cocoylbetaine | 2.5 |
| Ethylene glycol distearate | 1.5 |
| Polydimethylsiloxane of formula (II) sold by Wacker under the name SLM 28020 | 1.5 |
| Polydimethylsiloxane of viscosity 60 000 cSt (DC200-60 000 cSt from Dow Corning) | 1 |
| Hydroxyethylcellulose quaternized with 2,3-epoxypropyltrimethylammonium chloride, sold under the name Ucare Polymer JR-400 by the company Amerchol | 0.4 |
| Acrylic polymer in emulsion form, sold under the name Aqua SF1 by Noveon | 0.8 |

-continued

|  | in g AM |
|---|---|
| Preserving agents | qs |
| pH agentsqs | pH 5.0 |
| Demineralized waterqs | 100 |

Hair treated with this shampoo has long-lasting softness and smoothness.

Similar results are obtained by replacing the 1.5 g AM of polydimethylsiloxane of formula (II) with 1 g AM of polydimethylsiloxane of formula (I) sold by Wacker under the name Belsil ADM 652.

EXAMPLE 2

A rinse-out conditioner having the composition below was prepared:

| | |
|---|---|
| Cetyl alcohol | 3.7 g |
| Myristyl alcohol | 0.4 g |
| Hydroxyethylcellulose (Natrosol 250 HHR from Aqualon) | 0.25 g |
| Mixture of myristyl/cetyl/stearyl myristate/palmitate/stearate (Blanc de Baleine Végétal from Laserson) | 0.8 g |
| Cetyltrimethylammonium chloride as an aqueous solution containing 25% AM (Dehyquart ® A OR from Cognis) | 2.5 g (0.62 g AM) |
| Behenyltrimethylammonium chloride as a water/isopropanol solution comprising 80% AM (Genamin KDM-F from Clariant) | 0.6 g (0.48 g AM) |
| Polydimethylsiloxane of formula (II) sold by Wacker under the name SLM 28020 | 5 g (0.85 g AM) |
| Methosulphate (70/30 by weight) of dipalmitoylethylhydroxyethylmethylammonium/cetyl alcohol/stearyl alcohol (Dehyquart F 30 from Cognis) | 1 g |
| Citric acid | qs pH 3.5 ± 0.5 |
| Fragrance, preserving agents, | qs |
| Deionized water | qs 100 g |

Hair treated with this composition has long-lasting softness and smoothness.

EXAMPLE 3

A rinse-out conditioner having the composition below was prepared:

| | |
|---|---|
| Ethyltrimethylammonium methacrylate chloride homopolymer as a crosslinked inverse emulsion (Salcare SC 96 from Ciba) | 0.5 |
| Hydroxypropyl corn distarch phosphate | 3 |
| Oxyethylenated (40 EO) hydrogenated castor oil | 0.5 |
| Polydimethylsiloxane of formula (II) sold by Wacker under the name SLM 28020 | 2 |
| Fragrance | qs |
| Preserving agents | qs |
| Demineralized water | qs 100 g |

Hair treated with this conditioner has long-lasting softness and smoothness.

EXAMPLE 4

A rinse-out conditioner having the composition below was prepared:

| | in g AM |
|---|---|
| SMDI/polyethylene glycol polymer containing decyl end groups (Aculyn 44 from Rohm & Haas) | 1 |
| Ethyltrimethylammonium methacrylate chloride homopolymer as a crosslinked inverse emulsion (Salcare SC 96 from Ciba) | 0.2 |
| Oxyethylenated (40 EO) hydrogenated castor oil | 0.5 |
| Polydimethylsiloxane of formula (II) sold by Wacker under the name SLM 28020 | 2 |
| Fragrance | qs |
| Preserving agents | qs |
| Demineralized water | qs 100 g |

Hair treated with this composition has long-lasting softness and smoothness.

EXAMPLE 5

A leave-in care mousse presented in aerosol form was prepared from 95 g of the composition of Example 3 and 5 g of isobutane/propane/butane (56/24/20) propellant Propel 45 from the company Repsol.

Hair treated with this mousse has long-lasting softness and smoothness.

What is claimed is:

1. A cosmetic composition comprising, in a cosmetically acceptable medium, at least one conditioner chosen from synthetic oils, mineral oils, plant oils, fluoro oils and perfluoro oils, natural and synthetic waxes, compounds of ceramide type, carboxylic acid esters, silicones other than those of formulae (I) and (II), anionic polymers, nonionic polymers, cationic polymers, amphoteric polymers, cationic proteins, cationic protein hydrolysates and cationic surfactants and at least one aminosilicone chosen from aminosilicones of formulae (I) and (II) below:

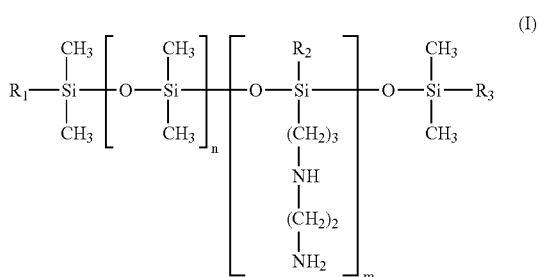

in which:
  m and n are numbers such that the sum (n+m) ranges from 1 to 1000,
  n is a number ranging from 0 to 999 and m is a number ranging from 1 to 1000;
  $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

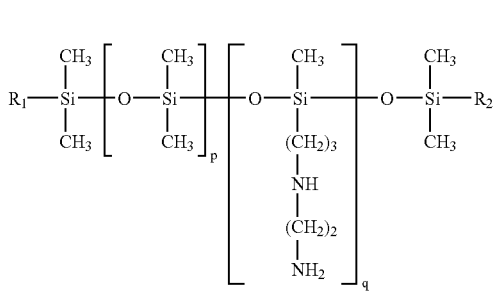

in which:
- p and q are numbers such that the sum (p+q) ranges from 1 to 1000,
- p is a number ranging from 0 to 999 and q is a number from 1 to 1000;
- $R_1$ and $R_2$, which may be identical or different, are chosen from hydroxyl and $C_1$-$C_4$ alkoxy radicals, wherein the at least one of the radicals $R_1$ and $R_2$ is chosen from $C_1$-$C_4$ alkoxy radicals.

2. The composition according to claim 1, wherein the synthetic oils are chosen from polyolefins of hydrogenated and non-hydrogenated polybutene types and polyolefins of hydrogenated and non-hydrogenated polydecene types.

3. The composition according to claim 1, wherein the plant oils are chosen from sunflower oil, corn oil, soybean oil, avocado oil, jojoba oil, marrow oil, grapeseed oil, sesame oil, hazelnut oil, fish oils, glyceryl tricaprocaprylate, and plant and animal oils of formula $R_9COOR_{10}$ wherein $R_9$ is chosen from higher fatty acid residues comprising from 7 to 29 carbon atoms and $R_{10}$ is chosen from linear and branched hydrocarbon-based chains comprising from 3 to 30 carbon atoms and natural and synthetic essential oils.

4. The composition according to claim 1, wherein the natural and synthetic waxes are chosen from carnauba wax, candelilla wax, alfalfa wax, paraffin wax, ozokerite, plant waxes, absolute waxes of flowers, animal waxes, marine waxes, polyethylene waxes and polyolefins.

5. The composition according to claim 1, wherein the compounds of ceramide type are chosen from:
- 2-N-linoleoylaminooctadecane-1,3-diol,
- 2-N-oleoylaminooctadecane-1,3-diol,
- 2-N-palmitoylaminooctadecane-1,3-diol,
- 2-N-stearoylaminooctadecane-1,3-diol,
- 2-N-behenoylaminooctadecane-1,3-diol,
- 2-N-aminooctadecane-1,3-diol,
- 2-N-[2-hydroxypalmitoyl]aminooctadecane-1,3-diol,
- 2-N-stearoylaminooctadecane-1,3,4-triol,
- 2-N-palmitoylaminohexadecane-1,3-diol,
- bis(N-hydroxyethyl-N-cetyl)malonamide,
- N-(2-hydroxyethyl)-N-(3-cetyloxy-2-hydroxypropyl) cetylamide,
- N-docosanoyl-N-methyl-D-glucamine and mixtures thereof.

6. The composition according to claim 1, wherein the carboxylic acid esters are chosen from ethyl and isopropyl palmitates, 2-ethylhexyl palmitate, 2-octyldecyl palmitate, alkyl myristates, hexyl stearate, butyl stearate, isobutyl stearate, dioctyl malate, hexyl laurate, 2-hexyldecyl laurate, isononyl isononanoate and cetyl octanoate.

7. The composition according to claim 1, wherein the silicones other than those of formulae (I) and (II) are chosen from non-volatile polyorganosiloxanes chosen from polyalkylsiloxanes, polyarylsiloxanes, polyalkylarylsiloxanes, silicone gums and silicone resins, polyorganosiloxanes modified with organofunctional groups, and mixtures thereof.

8. The composition according to claim 7, wherein:
(a) the polyalkylsiloxanes are chosen from:
- polydimethylsiloxanes comprising trimethylsilyl end groups;
- polydimethylsiloxanes comprising dimethylsilanol end groups; and
- poly($C_1$-$C_{20}$)alkylsiloxanes;

(b) the polyalkylarylsiloxanes are chosen from:
- linear and branched polydimethylmethylphenylsiloxanes; and
- polydimethyldiphenylsiloxanes with a viscosity ranging from $1\times10^{-5}$ to $5\times10^{-2}$ $m^2$/s at 25° C.;

(c) the silicone gums are chosen from polydiorganosiloxanes with number-average molecular masses ranging from 200,000 to 1,000,000, used alone or in the form of a mixture in a solvent;

(d) the silicone resins are chosen from resins comprising at least one unit chosen from units of $R_3SiO_{1/2}$, $R_2SiO_{2/2}$, $RSiO_{3/2}$ and $SiO_{4/2}$
in which R is chosen from hydrocarbon-based groups comprising from 1 to 16 carbon atoms and a phenyl group;

(e) the modified polyorganosiloxanes are chosen from silicones comprising at least one organofunctional group attached via a hydrocarbon-based radical.

9. The composition according to claim 8, wherein the silicone gums are chosen from:
- polydimethylsiloxane
- polydimethylsiloxane/methylvinylsiloxane,
- polydimethylsiloxane/diphenylsiloxane,
- polydimethylsiloxane/phenylmethylsiloxane,
- polydimethylsiloxane/diphenylsiloxane/methylvinylsiloxane, and the following mixtures:
- mixtures formed from a polydimethylsiloxane hydroxylated at the end of the chain and from a cyclic polydimethylsiloxane;
- mixtures formed from a polydimethylsiloxane gum and from a cyclic silicone; and
- mixtures of polydimethylsiloxanes of different viscosities.

10. The composition according to claim 7, wherein the polyorganosiloxanes modified with organofunctional groups are chosen from polyorganosiloxanes comprising at least one group chosen from:
a) polyethyleneoxy and polypropyleneoxy groups;
b) substituted and unsubstituted amine groups;
c) thiol groups;
d) alkoxylated groups;
e) hydroxyalkyl groups;
f) acyloxyalkyl groups;
g) alkylcarboxylic groups;
h) 2-hydroxyalkylsulphonate groups;
i) 2-hydroxyalkylthiosulphonate groups; and
j) hydroxyacylamino groups.

11. The composition according to claim 7, wherein the non-volatile polyorganosiloxanes are chosen from polyalkylsiloxanes comprising trimethylsilyl end groups, polyalkylsiloxanes comprising dimethylsilanol end groups, polyalkylarylsiloxanes, mixtures of two PDMSs comprising a gum and an oil of different viscosities, mixtures of organosiloxanes and of cyclic silicones, and polyorganosiloxane resins.

12. The composition according to claim 1, wherein the anionic polymers are chosen from:
polymers comprising carboxylic units derived from monomers chosen from unsaturated mono- and dicarboxylic acid monomers of the following formula:

in which n is an integer ranging from 0 to 10, $A_1$ is a methylene group, optionally connected to the carbon atom of the unsaturated group, or to the neighbouring methylene group when n is greater than 1, via a hetero atom, $R_1$ is chosen from a hydrogen atom and phenyl and benzyl groups, $R_2$ is chosen from a hydrogen atom and lower alkyl and carboxyl groups, $R_3$ is chosen from a hydrogen atom, lower alkyl groups and —$CH_2$—COOH, phenyl and benzyl groups;
polymers comprising units derived from sulphonic acids.

13. The composition according to claim 1, wherein the anionic polymers are chosen from:
acrylic acid copolymers;
copolymers derived from crotonic acid;
polymers derived from entities chosen from maleic, fumaric and itaconic acids and anhydrides with vinyl esters, vinyl ethers, vinyl halides and phenylvinyl derivatives, acrylic acid and its esters;
copolymers of methacrylic acid and of methyl methacrylate;
the copolymer of methacrylic acid and of ethyl acrylate;
vinyl acetate/crotonic acid copolymer; and
vinyl acetate/croton acid/polyethylene glycol terpolymer.

14. The composition according to claim 1, wherein the amphoteric polymers are chosen from polymers comprising at least one unit derived from:
a) at least one monomer chosen from acrylamides and methacrylamides substituted on the nitrogen with a radical chosen from alkyl radicals,
b) at least one acidic comonomer comprising at least one reactive carboxylic group, and
c) at least one basic comonomer.

15. The composition according to claim 14, wherein in (c), the at least one basic comonomer is chosen from esters comprising primary, secondary, tertiary and quaternary amine substituents of acrylic and methacrylic acids and the product of quaternization of dimethylaminoethyl methacrylate with a sulphate chosen from dimethyl and diethyl sulphates.

16. The composition according to claim 1, wherein the nonionic polymers are chosen from:
polyalkyloxazolines;
vinyl acetate homopolymers;
copolymers of vinyl acetate and acrylic ester;
copolymers of vinyl acetate and ethylene;
copolymers of vinyl acetate and maleic ester;
copolymers of polyethylene and maleic anhydride;
alkyl acrylate homopolymers and alkyl methacrylate homopolymers;
acrylic ester copolymers;
copolymers of acrylonitrile and a nonionic monomer; and
copolymers of alkyl acrylate and of urethane.

17. The composition according to claim 1, wherein the cationic polymers are chosen from polymers comprising units comprising at least one amine group chosen from primary, secondary, tertiary and quaternary amine groups that either form part of the main polymer chain or are borne by a side substituent directly attached to the main polymer chain.

18. The composition according to claim 17, wherein the cationic polymers are chosen from cationic cyclopolymers, cationic polysaccharides, and quaternary polymers of vinylpyrrolidone and of vinylimidazole and mixtures thereof.

19. The composition according to claim 18, wherein the cationic polysaccharides are chosen from hydroxyethylcelluloses that have reacted with an epoxide substituted with a trimethylammonium group.

20. The composition according to claim 18, wherein the cationic polysaccharides are chosen from guar gums modified with a 2,3-epoxypropyltrimethylammonium salt.

21. The composition according to claim 1, wherein the cationic surfactants are chosen from:
A) the quaternary ammonium salts of general formula (XXIII) below:

wherein $X^-$ is an anion chosen from halides, ($C_2$-$C_6$) alkyl suiphates, phosphates, and alkyl and alkylaryl sulphonates, and anions derived from organic acids, and
i) the radicals $R_1$, $R_2$, and $R_3$, which may be identical or different, are chosen from linear and branched aliphatic radicals comprising from 1 to 4 carbon atoms, and aromatic radicals;
$R_4$ is chosen from linear and branched alkyl radicals comprising from 16 to 30 carbon atoms; or
ii) the radicals $R_1$ and $R_2$, which may be identical or different, are chosen from linear and branched aliphatic radicals comprising from 1 to 4 carbon atoms, and aromatic radicals;
$R_3$ and $R_4$, which may be identical or different, are chosen from linear and branched alkyl radicals comprising from 12 to 30 carbon atoms, wherein the alkyl radicals comprise at least one function chosen from ester and amide functions;
B) the quaternary ammonium salts of imidazolinium;
C) the diquaternary ammonium salts of formula (XXV):

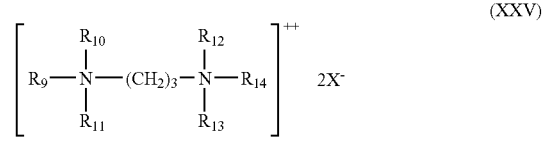

in which
$R_9$ is chosen from aliphatic radicals comprising from 16 to 30 carbon atoms,
$R_{10}$, $R_{11}$, $H_{12}$, $H_{13}$ and $R_{14}$, which may be identical or different, are chosen from hydrogen and alkyl radicals comprising from 1 to 4 carbon atoms, and
$X^-$ is an anion chosen from halides, acetates, phosphates, nitrates and methyl suiphates;
D) the quaternary ammonium salts comprising at least one ester function, of formula (XXVI) below:

$$R_{17}-\overset{O}{\underset{\|}{C}}-(OC_nH_{2n})_y-\overset{(C_rH_{2r}O)_z-R_{18}}{\underset{R_{15}}{\overset{|}{N^+}}}-(C_pH_{2p}O)_x-R_{16}, \quad X^- \tag{XXVI}$$

in which:
   $R_{15}$ is chosen from $C_1$-$C_6$ alkyl radicals and $C_1$-$C_6$, hydroxyalkyl and dihydroxyalkyl radicals;
   $R_{16}$ is chosen from:
      a radical $$R_{19}-\overset{O}{\underset{\|}{C}}-$$

linear and branched, saturated and unsaturated $C_1$-$C_{22}$ hydrocarbon-based radicals $R_{20}$, and
      a hydrogen atom,
   $R_{18}$ is chosen from:
      a radical $$R_{21}-\overset{O}{\underset{\|}{C}}-$$

linear and branched, saturated and unsaturated $C_1$-$C_6$ hydrocarbon-based radicals $R_{22}$, and
      a hydrogen atom,
   $R_{17}$, $R_{19}$ and $R_{21}$, which may be identical or different, are chosen from linear and branched, saturated and unsaturated $C_7$-$C_{21}$ hydrocarbon-based radicals;
   n, p and r, which may be identical or different, are chosen from integers ranging from 2 to 6;
   y is chosen from integers ranging from 1 to 10;
   x and z, which may be identical or different, are chosen from integers ranging from 0 to 10;
   $X^-$ is an anion chosen from simple and complex, organic and inorganic anions;
with the proviso that the sum x+y+z is from 1 to 15, that when x is 0, then $R_{16}$ is $R_{20}$ and that when z is 0, then $R_{18}$ is $R_{22}$.

22. The composition according to claim 21, wherein, in A) the cationic surfactant is a stearamidopropyldimethyl(myristyl acetate)ammonium salt.

23. The composition according to claim 21, wherein in B) the quaternary ammonium salts of imidazolinium are chosen from those of formula (XXIV) below:

$$\left[\begin{array}{c} R_6 \\ \diagup \\ N \overset{}{=} \underset{R_7}{\overset{}{N}}-CH_2-CH_2-N(R_8)-CO-R_5 \end{array}\right]^+ \quad X^- \tag{XXIV}$$

in which
   $R_5$ is chosen from alkenyl and alkyl radicals comprising from 8 to 30 carbon atoms,
   $R_6$ is chosen from a hydrogen atom, $C_1$-$C_4$ alkyl radicals and alkenyl and alkyl radicals comprising from 8 to 30 carbon atoms,
   $R_7$ is chosen from $C_1$-$C_4$ alkyl radicals,
   $R_8$ is chosen from a hydrogen atom and $C_1$-$C_4$ alkyl radicals, and
   $X^-$ is an anion chosen from halides, phosphates, acetates, lactates, alkyl suiphates, alkyl suiphonates and alkylaryl sulphonates.

24. A method for washing or caring for a keratin material comprising applying to the keratin material a composition comprising, in a cosmetically acceptable medium, at least one conditioner and at least one aminosilicone chosen from aminosilicones of formulae (I) and (II) below:

$$R_1-\underset{CH_3}{\overset{CH_3}{\underset{|}{\overset{|}{Si}}}}-O-\left[\underset{CH_3}{\overset{CH_3}{\underset{|}{\overset{|}{Si}}}}-O\right]_n-\left[\underset{(CH_2)_3}{\overset{R_2}{\underset{|}{\overset{|}{Si}}}}-O\right]_m-\underset{CH_3}{\overset{CH_3}{\underset{|}{\overset{|}{Si}}}}-R_3 \tag{I}$$

$$\begin{array}{c} | \\ NH \\ | \\ (CH_2)_2 \\ | \\ NH_2 \end{array}$$

in which:
   m and n are numbers such that the sum (n+m) ranges from 1 to 1000,
   n is a number ranging from 0 to 999 and m is a number ranging from 1 to 1000;
   $R_1$, $R_2$ and $R_3$, which may be identical or different, are chosen from hydroxyl and $C_1$-$C_4$ alkoxy radicals, wherein at least one of the radicals $R_1$, $R_2$, and $R_3$, is chosen from $C_1$-$C_4$ alkoxy radicals; and $$R_1-\underset{CH_3}{\overset{CH_3}{\underset{|}{\overset{|}{Si}}}}-O-\left[\underset{CH_3}{\overset{CH_3}{\underset{|}{\overset{|}{Si}}}}-O\right]_p-\left[\underset{(CH_2)_3}{\overset{CH_3}{\underset{|}{\overset{|}{Si}}}}-O\right]_q-\underset{CH_3}{\overset{CH_3}{\underset{|}{\overset{|}{Si}}}}-R_2 \tag{II}$$

$$\begin{array}{c} | \\ NH \\ | \\ (CH_2)_2 \\ | \\ NH_2 \end{array}$$

in which:
   and q are numbers such that the sum (p+q) ranges from 1 to 1000,
   is a number ranging from 0 to 999 and q is a number from 1 to 1000;
   $R_1$, and $R_2$, which may be identical or different, are chosen from hydroxyl and $C_1$-$C_4$ alkoxy radicals, wherein the at least one of the radicals $R_1$, and $R_2$ is chosen from $C_1$-$C_4$ alkoxy radicals.

25. A process for treating a keratin material, comprising applying to the keratin material a cosmetic composition comprising, in a cosmetically acceptable medium, at least one conditioner and at least one aminosilicone chosen from aminosilicones of formulae (I) and (II) below:

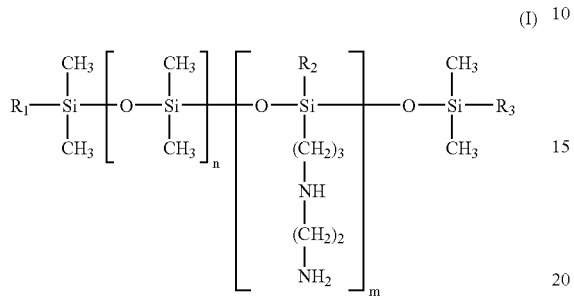

in which:
- m and n are numbers such that the sum (n+m) ranges from 1 to 1000,
- n is a number ranging from 0 to 999 and m is a number ranging from 1 to 1000;
- $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

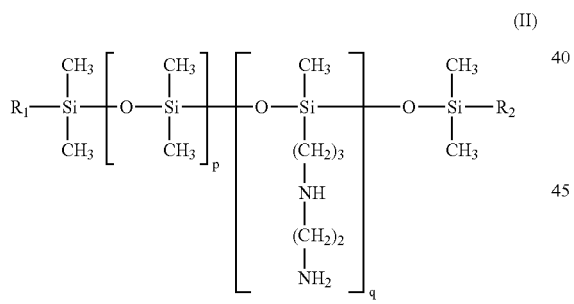

in which:
- p and q are numbers such that the sum (p+q) ranges from 1 to 1000,
- p is a number ranging from 0 to 999 and q is a number from 1 to 1000;
- $R_1$ and $C_2$, which may be identical or different, are chosen from hydroxyl and $C_1$-$C_4$ alkoxy radicals, wherein the at least one of the radicals $R_1$ and $R_2$ is chosen from $C_1$-$C_4$ alkoxy radicals, and then optionally rinsing the keratin material with water.

26. The process according to claim 25, wherein the keratin material is hair.

27. A process for conditioning a keratin material comprising applying to the keratin material a composition comprising, in a cosmetically acceptable medium, at least one conditioner and at least one aminosilicone chosen from aminosilicones of formulae (I) and (II) below:

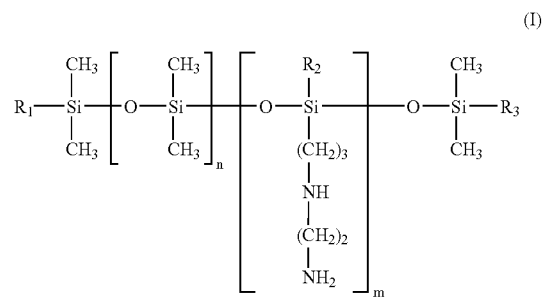

in which:
- m and n are numbers such that the sum (n+m) ranges from 1 to 1000,
- n is a number ranging from 0 to 999 and m is a number ranging from 1 to 1000;
- $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

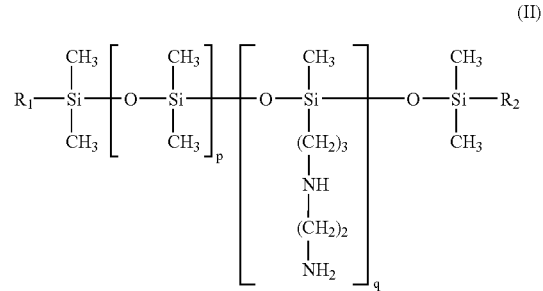

in which:
- p and q are numbers such that the sum (p+q) ranges from 1 to 1000,
- p is a number ranging from 0 to 999 and q is a number from 1 to 1000;
- $R_1$ and $R_2$, which may be identical or different, are chosen from hydroxyl and $C_1$-$C_4$ alkoxy radicals, wherein the at least one of the radicals $R_1$ and $R_2$ is chosen from $C_1$-$C_4$ alkoxy radicals.

28. A method for improving lightness, softness, sheen and/or disentangling, and/or facilitating styling of a keratin material, comprising applying to the keratin material a composition comprising, in a cosmetically acceptable medium, at least one conditioner and at least one aminosilicone chosen from aminosilicones of formulae (I) and (II) below:

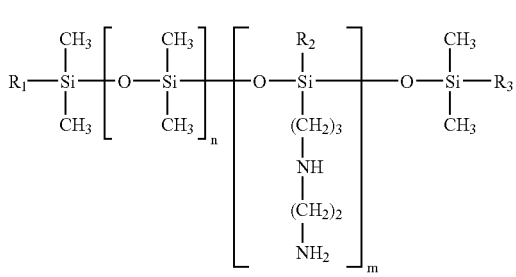

in which:
  m and n are numbers such that the sum (n+m) ranges from 1 to 1000,
  n is a number ranging from 0 to 999 and m is a number ranging from 1 to 1000;
  $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

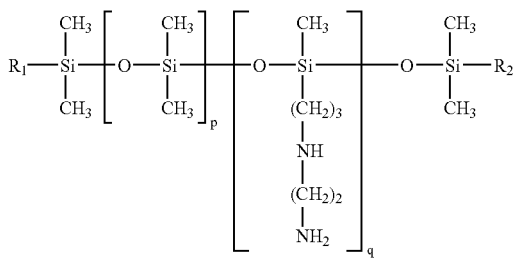

in which:
  p and q are numbers such that the sum (p+q) ranges from 1 to 1000,
  p is a number ranging from 0 to 999 and q is a number from 1 to 1000;
  $R_1$, and $R_2$, which may be identical or different, are chosen from hydroxyl and $C_1$-$C_4$ alkoxy radicals, wherein the at least one of the radicals $R_1$ $R_2$ is chosen from $C_1$-$C_4$ alkoxy radicals.

29. A method for improving remanence of the conditioning effects with respect to shampooing, comprising including in a composition at least one conditioner and at least one aminosilicone chosen from aminosilicones of formulae (I) and (II) below:

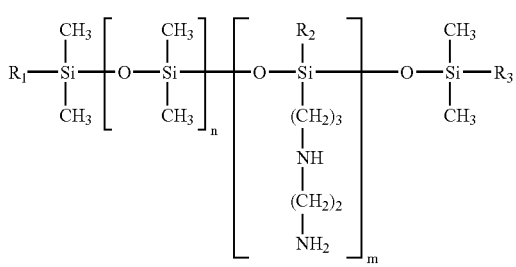

in which:
  m and n are numbers such that the sum (n+m) ranges from 1 to 1000,
  n is a number ranging from 0 to 999 and m is a number ranging from 1 to 1000;
  $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

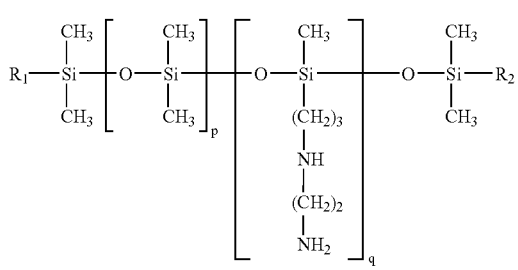

in which:
  p and q are numbers such that the sum (p+q) ranges from 1 to 1000,
  p is a number ranging from 0 to 999 and q is a number from 1 to 1000;
  $R_1$ and $R_2$, which may be identical or different, are chosen from hydroxyl and $C_1$-$C_4$ alkoxy radicals, wherein the at least one of the radicals $R_1$ and $R_2$ is chosen from $C_1$-$C_4$ alkoxy radicals.

30. A composition for improving remanence of the conditioning effects with respect to shampooing, comprising, in a cosmetically acceptable medium, at least one conditioner and at least one aminosilicone chosen from aminosilicones of formulae (I) and (II) below:

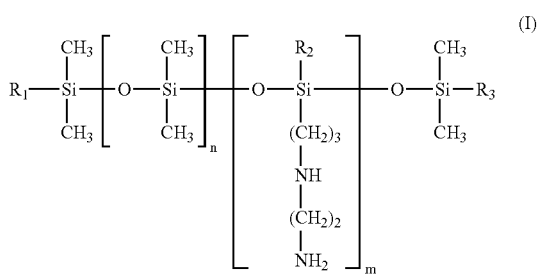

in which:
  m and n are numbers such that the sum (n+m) ranges from 1 to 1000,
  n is a number ranging from 0 to 999 and m is a number ranging from 1 to 1000;
  $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

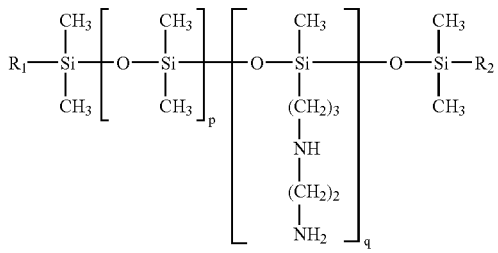

(II)

in which:
- p and q are numbers such that the sum (p+q) ranges from 1 to 1000,
- p is a number ranging from 0 to 999 and q is a number from 1 to 1000;
- $R_1$ and $R_2$, which may be identical or different, are chosen from hydroxyl and $C_1$-$C_4$ alkoxy radicals, wherein the at least one of the radicals $R_1$ and $R_2$ is chosen from $C_1$-$C_4$ alkoxy radicals;
- wherein the composition is effective in improving remanence of the conditioning effects with respect to shampooing.

31. A process for improving remanence of conditioning effects of a cosmetic composition with respect to shampooing, comprising including in said composition at least one aminosilicone, wherein the at least one aminosilicone chosen from aminosilicones of formulae (I) and (II) below:

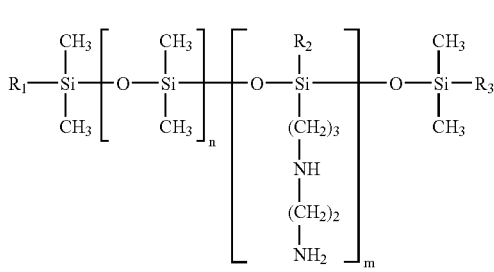

(I)

in which:
- m and n are numbers such that the sum (n+m) ranges from 1 to 1000,
- n is a number ranging from 0 to 999 and m is a number ranging from 1 to 1000;
- $R_1$, $R_2$ and $R_3$, which may be identical or different, are chosen from hydroxyl and $C_1$-$C_4$ alkoxy radicals, wherein at least one of the radicals $R_1$, $R_2$ and $R_3$ is chosen from $C_1$-$C_4$ alkoxy radicals; and

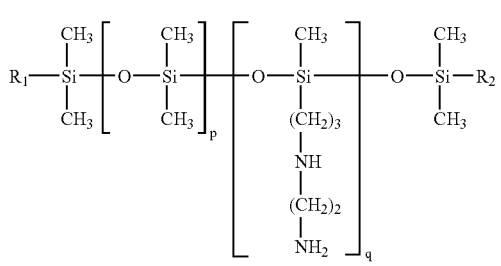

(II)

in which:
- p and q are numbers such that the sum (p+q) ranges from 1 to 1000,
- p is a number ranging from 0 to 999 and q is a number from i to 1000;
- $R_1$ and $R_2$, which may be identical or different, are chosen from hydroxyl and $C_1$-$C_4$ alkoxy radicals, wherein the at least one of the radicals $R_1$ and $R_2$ is chosen from $C_1$-$C_4$ alkoxy radicals.

32. The composition according to 17 wherein the cationic polymers are chosen from crosslinked methacryloyloxy($C_1$-$C_4$)alkyltri($C_1$-$C_4$)alkylammonium salt polymers.

33. The composition according to claim 3, wherein $R_{10}$ is chosen from alkyl and alkenyl radicals.

\* \* \* \* \*

UNITED STATES PATENT AND TRADEMARK OFFICE
CERTIFICATE OF CORRECTION

| | |
|---|---|
| PATENT NO. | : 7,485,289 B2 |
| APPLICATION NO. | : 11/706399 |
| DATED | : February 3, 2009 |
| INVENTOR(S) | : Jonathan Gawtrey et al. |

It is certified that error appears in the above-identified patent and that said Letters Patent is hereby corrected as shown below:

Claim 5, col. 39, line 49,
delete "2-N-aminooctadecane-1,3-diol".

Claim 10, col. 40, line 57,
"h) 2-hydroxyalkylsuiphonate groups;" should read
--h) 2-hydroxyalkylsulphonate groups;--.

Claim 21, col. 42, line 29,
"suiphates" should read --sulphates--.

Claim 21, col. 42, line 65,
"suiphates" should read --sulphates--.

Claim 23, col. 44, line 5,
"alkyl suiphates, alkyl suiphonates" should read
--alkyl sulphates, alkyl sulphonates--.

Claim 24, col. 44, line 59,
"and q are numbers" should read --p and q are numbers--.

Claim 24, col. 44, line 61, "is a number" should read
--p is a number--.

Claim 25, col. 45, line 59,
"$R_1$ and $C_2$" should read --$R_1$ and $R_2$--.

UNITED STATES PATENT AND TRADEMARK OFFICE
CERTIFICATE OF CORRECTION

PATENT NO. : 7,485,289 B2
APPLICATION NO. : 11/706399
DATED : February 3, 2009
INVENTOR(S) : Jonathan Gawtrey et al.

It is certified that error appears in the above-identified patent and that said Letters Patent is hereby corrected as shown below:

Claim 28, col. 47, line 46,
"$R_1 R_2$" should read --$R_1$ and $R_2$--.

Claim 31, col. 50, line 33,
"ito 1000;" should read --to 1000--.

Signed and Sealed this

Seventh Day of April, 2009

JOHN DOLL
*Acting Director of the United States Patent and Trademark Office*